(12) United States Patent
Koehler et al.

(10) Patent No.: US 8,273,743 B2
(45) Date of Patent: Sep. 25, 2012

(54) QUINOXALINE INHIBITORS OF THE HEDGEHOG SIGNALLING

(75) Inventors: Michael F. T. Koehler, Burlingame, CA (US); Richard Goldsmith, Belmont, CA (US); Daniel P. Sutherlin, South San Francisco, CA (US)

(73) Assignees: Curis, Inc., Lexington, MA (US); Genentech, Inc., South San Francisco, CA (US)

( * ) Notice: Subject to any disclaimer, the term of this patent is extended or adjusted under 35 U.S.C. 154(b) by 1419 days.

(21) Appl. No.: 11/587,963

(22) PCT Filed: Apr. 29, 2005

(86) PCT No.: PCT/US2005/015121
§ 371 (c)(1), (2), (4) Date: Sep. 6, 2007

(87) PCT Pub. No.: WO2006/078283
PCT Pub. Date: Jul. 27, 2006

(65) Prior Publication Data
US 2008/0261989 A1      Oct. 23, 2008

Related U.S. Application Data

(60) Provisional application No. 60/566,843, filed on Apr. 30, 2004.

(51) Int. Cl.
*A61K 31/495* (2006.01)
*A61K 31/44* (2006.01)

(52) U.S. Cl. ......... 514/249; 514/303; 544/350; 544/353

(58) Field of Classification Search .................. 514/249, 514/303; 544/350, 353
See application file for complete search history.

(56) References Cited

U.S. PATENT DOCUMENTS
5,657,141 A * 8/1997 Terada et al. ................. 349/184

FOREIGN PATENT DOCUMENTS
GB       1198301 A        7/1970
WO    WO 03/088970 A    10/2003

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Buu-Hoi, et al. Bulletin de la Societe Chimique de France, 1950, 753-757.*
Database Chemcast Chemical Abstracts Service, Columbus, Ohio, US; XP002388654, retrieved from STN Database Acession No. 2003:2907033 Order No. 4705-0239, Apr. 25, 2003, Chemdiv, Inc.

Gazit A. et al., Tyrphostins. 5. Potent Inhibitors of Platelet Derived Growth Factor Receptor Tyrosine Kinase: Structure Activity Relationships in Quinoxalines, Quinolines and Indole Tyrphostins, Journal of Medicinal Chemistry, vol. 39, 1996, pp. 2170-2177.
Cavallini G., New Antiviral Compounds with Considerable Activity in Vivo. IV. Aromatic Apha-Keto Aldehydes, Journal of Medicinal Chemistry vol. 7, No. 3, May 1964, pp. 255-258.
Piras S. et al.. Quinoxaline Chemistry. Part 6 Synthesis and evaluation of antiulcer and gastroprotective activity of 2-[arylmethylmercapto-arylmethylsulfinyl, piperazinyl1-3-R-substituted]quinoxalines IL Farmaco, vol. 51, No. 8/9, 1996, pp. 569-577.
Sarodnick G. et al, Hetarylchinoxaline als Thiabendazolanaloge Pharmaziem, vol. 38, No. 12, 1983, pp. 829-832.
Buu-Hoi N G et al. Sulfanilamides derives de la 2-phenylquinoxaline Bulletin De LA Societe Chimique De France, 1950, pp. 753-757.
Schubert H et al, Synthesis von kristallin-flussigen Verbindungen. I. n-Alkyl-und n-Alkoxyderivate des 3-Hydroxy-2, 5-diphenyl-pyrazins, Journal fur Praktische Chemie, vol. 33, 1966, pp. 265-276.
Brzozowsli Z: 2-Mercapto-N-(azolyl) Benzenesulphonamides III. Synthesis of some new 2-mercapto-N-(5-amino-1, 2, 4-triazol-3-yl) Benzenesulphonamide derivatives with potential anti-HIV or anti-cancer activity ACTA Polaniae Pharmaceutica, vol. 53, No. 4, 1996, pp. 269-276.
Casellato V. et al : Analisi di gliossali aromatici. Reazione di cannizzaro e determinazione spettrofotometrica, Bolletino Chimico Farmaceutico, vol. 105, 1996, pp. 880-890.

(Continued)

Primary Examiner — Douglas M Willis
(74) Attorney, Agent, or Firm — Millen, White, Zelano & Branigan, P.C.

(57) ABSTRACT

The invention provides novel inhibitors of hedgehog signaling that are useful as a therapeutic agents for treating malignancies where the compounds have the general formula I:

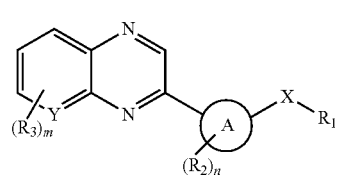

wherein A is a carbocycle or heterocycle; X is alkylene, $NR_4C(O)$, $NR_4C(S)$, $NR_4C(NH)$, $NR_4SO$, $NR_4SO_2$, $NR_4C(O)NH$, $NR_4C(S)NH$, $C(O)NR_4$, $C(S)NR_4$, $C(NH)NR_4$, $NR_4PO$ or $NR_4PO(OH)$ wherein $R_4$ is H or alkyl; $R_1$ is selected from the group consisting of alkyl, cycloalkyl, aryl or a heterocycle each of which is optionally substituted with hydroxy, halogen, amino, nitro, alkyl, acyl, alkylsulfonyl or alkoxy; $R_2$ is halogen, hydroxy, alkyl, acyl or alkoxy each optionally substituted with hydroxy, halogen, amino, nitro, alkyl, acyl, alkylsulfonyl or alkoxy; $R_3$ is halogen, hydroxy, alkyl, acyl or alkoxy each optionally substituted with hydroxy, halogen, amino, nitro, alkyl, acyl, alkylsulfonyl or alkoxy; m is 0-3; n is 0-3; and salts and solvates thereof. The invention also provides methods of using these compounds for therapy and/or prophylaxis in a mammal of hyperproliferative diseases and angiogenesis mediated diseases due to their activity for inhibiting the hedgehog signaling pathway.

31 Claims, No Drawings

OTHER PUBLICATIONS

Jigajinni, V.B., et al., "Structure—Property Relationships in PMR-15-Type Polymide Resins: III. New Polymides Incorporating Triazoles, Quinoxalines, Pyridopyrazines and Pyrazinopyridazines," High Perform. Polym., 5 (1993), pp. 239-257.

Rusanov, A.L., et al., Vysokomolekulyarnye Soedineniya, Seriya B: Kratkie Soobshcheniya (1993), 35(9), 1518—20, Published in: Vysokomol. Soedin., Ser. B, 35(9), Abstract and 10 disclosed structures.

Akutsu, F., et al., "Synthesis and Characterization of Novel Aromatic Polyamides and Polyimides Derived from 2,3-Di(3-aminophenyl)quinoxaline," Polymer Journal, vol. 29, No. 6, pp. 529-533 (1997).

Rusanov, A.L., et al., "New Polymers Based on Quinoxaline-Containing Monomers," Nesmeyanov Inst. Organoelemt. Comp., Moscow, 117813—Abstract, 1993.

* cited by examiner

QUINOXALINE INHIBITORS OF THE HEDGEHOG SIGNALLING

This non-provisional application claims priority to provisional U.S. application 60/566,843 filed on 30 Apr. 2004, the entire disclosure of which is incorporated herein by reference.

FIELD OF THE INVENTION

The present invention relates to organic compounds useful for therapy and/or prophylaxis in a mammal, in particular to quinoxaline compounds that inhibit the hedgehog signaling pathway and are useful in the treatment of hyperproliferative diseases and angiogenesis mediated diseases.

BACKGROUND OF THE INVENTION

Hedgehog (Hh) protein was first identified in *Drosophila melanogaster* as a segment-polarity gene involved in embryo patterning (Nusslein-Volhard et al., Roux. Arch. Dev. Biol. 193: 267-282 (1984)). Three orthologs of *Drosophila* hedgehog (Sonic, Desert and Indian) were later identified to occur in all vertebrates including fish, birds and mammals. Desert hedgehog (DHh) is expressed principally in the testes, both in mouse embryonic development and in the adult rodent and human; Indian hedgehog (IHh) is involved in bone development during embryogenesis and in bone formation in the adult; and, Sonic hedgehog (SHh) is expressed at high levels in the notochord and floor plate of developing vertebrate embryos. In vitro explant assays as well as ectopic expression of SHh in transgenic animals have show that SHh plays a key role in neuronal tube patterning (Echelard et al., supra.; Ericson et al., Cell 81: 747-56 (1995); Marti et al., Nature 375: 322-5 (1995); Krauss et al., Cell 75, 1432-44 (1993); Riddle et al., Cell 75: 1401-16 (1993); Roelink et al, Cell 81:445-55 (1995); Hynes et al., Neuron 19: 15-26 (1997)). Hh also plays a role in the development of limbs (Krauss et al., Cell 75: 1431-44 (1993); Laufer et al., Cell 79, 993-1003 (1994)), somites (Fan and Tessier-Lavigne, Cell 79, 1175-86 (1994); Johnson et al., Cell 79: 1165-73 (1994)), lungs (Bellusci et al., Develop. 124: 53-63 (1997) and skin (Oro et al., Science 276: 817-21 (1997)). Likewise, IHh and DHh are involved in bone, gut and germinal cell development (Apelqvist et al., Curr. Biol. 7: 801-4 (1997); Bellusci et al., Dev. Suppl. 124: 53-63 (1997); Bitgood et al., Curr. Biol. 6: 298-304 (1996); Roberts et al., Development 121: 3163-74 (1995)).

Human SHh is synthesized as a 45 kDa precursor protein that upon autocatalytic cleavage yields a 20 kDa N-terminal fragment that is responsible for normal hedgehog signaling activity; and a 25 kDa C-terminal fragment that is responsible for autoprocessing activity in which the N-terminal fragment is conjugated to a cholesterol moiety (Lee, J. J., et al. (1994) Science 266, 1528-1536; Bumcrot, D. A., et al. (1995), Mol. Cell. Biol. 15, 2294-2303; Porter, J. A., et al. (1995) Nature 374, 363-366). The N-terminal fragment consists of amino acid residues 24-197 of the full-length precursor sequence which remains membrane-associated through the cholesterol at its C-terminus (Porter, J. A., et al. (1996) Science 274, 255-258; Porter, J. A., et al. (1995) Cell 86, 21-34). Cholesterol conjugation is responsible for the tissue localization of the hedgehog signal.

At the cell surface, the Hh signal is thought to be relayed by the 12 transmembrane domain protein Patched (Ptc) (Hooper and Scott, Cell 59: 751-65 (1989); Nakano et al., Nature 341: 50S-13 (1989)) and the G-protein-coupled-like receptor Smoothened (Smo) (Alcedo et al., Cell 86: 221-232 (1996); van den Heuvel and Ingham, Nature 382: 547-551 (1996)). Both genetic and biochemical evidence support a receptor model where Ptch and Smo are part of a multicomponent receptor complex (Chen and Struhl, Cell 87: 553-63 (1996); Marigo et al., Nature 384: 176-9 (1996); Stone et al., Nature 384: 129-34 (1996)). Upon binding of Hh to Ptch, the normal inhibitory effect of Ptch on Smo is relieved, allowing Smo to transduce the Hh signal across the plasma membrane. However, the exact mechanism by which Ptch controls Smo activity still has yet to be clarified.

The signaling cascade initiated by Smo results in activation of Gli transcription factors that translocate into the nucleus where they control transcription of target genes. Gli has been shown to influence transcription of Hh pathway inhibitors such as Ptc and Hip1 in a negative feedback loop indicating that tight control the Hh pathway activity is required for proper cellular differentiation and organ formation. Uncontrolled activation of Hh signaling pathway are associated with malignancies in particular those of the brain, skin and muscle as well as angiogenesis. An explanation for this is that Hh pathway has been shown to regulate cell proliferation in adults by activation of genes involved in cell cycle progression such as cyclin D which is involved in G1-S transition. Also, SHh blocks cell-cycle arrest mediated by p21, an inhibitor of cyclin dependent kinases. Hh signaling is further implicated in cancer by inducing components in the EGFR pathway (EGF, Her2) involved in proliferation as well as components in the PDGF (PDGFα) and VEGF pathways involved in angiogenesis. Loss of function mutations in the Ptch gene have been identified in patients with the basal cell nevus syndrome (BCNS), a hereditary disease characterized by multiple basal cell carcinomas (BCCs). Dysfunctional Ptch gene mutations have also been associated with a large percentage of sporadic basal cell carcinoma tumors (Chidambaram et al., Cancer Research 56: 4599-601 (1996); Gailani et al., Nature Genet. 14: 78-81 (1996); Hahn et al., Cell 85: 841-51 (1996); Johnson et al., Science 272: 1668-71 (1996); Unden et al., Cancer Res. 56: 4562-5; Wicking et al., Am. J. Hum. Genet. 60: 21-6 (1997)). Loss of Ptch function is thought to cause an uncontrolled Smo signaling in basal cell carcinoma. Similarly, activating Smo mutations have been identified in sporadic BCC tumors (Xie et al., Nature 391: 90-2 (1998)), emphasizing the role of Smo as the signaling subunit in the receptor complex for SHh.

Various inhibitors of hedgehog signaling have been investigated such as Cyclopamine, a natural alkaloid that has been shown to arrest cell cycle at G0-G1 and to induce apoptosis in SCLC. Cyclopamine is believed to inhibit Smo by binding to its heptahelical bundle. Forskolin has been shown to inhibit the Hh pathway downstream from Smo by activating protein kinase A (PKA) which maintains Gli transcription factors inactive. Despite advances with these and other compounds, there remains a need for potent inhibitors of the hedgehog signaling pathway.

SUMMARY OF THE INVENTION

In one aspect of the present invention there is provided novel hedgehog inhibitors having the general formula (I)

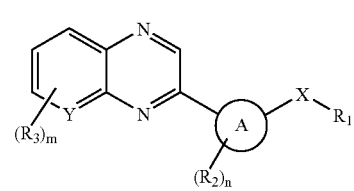

I wherein

A is a carbocycle or heterocycle;

X is alkylene, $NR_4C(O)$, $NR_4C(S)$, $NR_4C(NH)$, $NR_4SO$, $NR_4SO_2$, $NR_4C(O)NH$, $NR_4C(S)NH$, $C(O)NR_4$, $C(S)NR_4$, $C(NH)NR_4$, $NR_4PO$ or $NR_4PO(OH)$ wherein $R_4$ is H or alkyl;

Y is N, CH or $CR_3$;

$R_1$ is selected from the group consisting of alkyl, cycloalkyl, aryl or a heterocycle each of which is optionally substituted with hydroxyl, halogen, amino, nitro, alkyl, acyl, alkylsulfonyl, haloalkyl or alkoxy; and said cycloalkyl, aryl and heterocycle are optionally further substituted with —$(CH_2)_s$—$(O)_u$—$(CH_2)_t$-Z wherein Q is C(O), S(O), $SO_2$, C(O)O, OC(O), $NR_4C(O)$, $NR_4C(S)$, $NR_4SO$, $NR_4SO_2$, $NR_4C(O)NH$, $NR_4C(S)NH$, $C(O)NR_4$, or $C(S)NR_4$; and Z is hydroxyl, amino, halogen, alkylsulfonly, alkoxy, alkoxycarbonyl, haloalkyl, a carbocycle, a heterocycle or a carbocycle or heterocycle substituted with hydroxyl, halogen, amino, nitro, alkyl, acyl, alkylsulfonyl, haloalkyl, hydroxyalkyl, alkoxy or alkoxyalkoxy; and s and t are independently 0 to 5 and u is 0 or 1;

$R_2$ is halogen, hydroxyl, alkyl, acyl or alkoxy each optionally substituted with hydroxyl, halogen, amino, nitro, alkyl, acyl, alkylsulfonyl or alkoxy;

$R_3$ is halogen, hydroxyl, alkyl, acyl or alkoxy each optionally substituted with hydroxyl, halogen, amino, nitro, alkyl, acyl, alkylsulfonyl or alkoxy; m is 0-3;

n is 0-3;

and salts and solvates thereof.

In another aspect of the invention, there are provided compositions comprising compounds of formula I and a carrier, diluent or excipient.

In another aspect of the invention, there is provided a method for treating cancer comprising administering an effective amount of a compound of formula I to a mammal in need thereof.

In another aspect of the invention, there is provided a method for inhibiting hedgehog signaling in a cell comprising contacting said cell with a compound of formula I.

In another aspect of the invention, there is provided a method for treating a disease or condition associated with the hedgehog signaling in a mammal, comprising administering to said mammal an effective amount of a compound of formula I.

DETAILED DESCRIPTION OF THE PREFERRED EMBODIMENTS

Definitions

"Acyl" means a carbonyl containing substituent represented by the formula —C(O)—R in which R is alkyl, a carbocycle, a heterocycle, carbocyclealkyl or heterocycle alkyl wherein alkyl, carbocycle and heterocycle are as herein defined. Acyl groups include alkanoyl (e.g. acetyl), aroyl (e.g. benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion may be saturated hydrocarbon chain, however also includes unsaturated hydrocarbon carbon chains such as "alkenylamino" and "alkynylamino. Examples of alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted alkyl groups may contain one, two, three or four substituents which may be the same or different. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Substituted alkyls include substituted methyls e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" denotes the group —C(NH)—NHR wherein R is H or alkyl or aralkyl. A particular amidine is the group —NH—C(NH)—$NH_2$.

"Amino" denotes primary (i.e. —$NH_2$), secondary (i.e. —NRH) and tertiary (i.e. —NRR) amines. Secondary and tertiary amines include alkylamine, dialkylamine, arylamine, diarylamine, aralkylamine and diaralkylamine. Particular secondary and tertiary amines are methylamine, ethylamine, propylamine, isopropylamine, phenylamine, benzylamine dimethylamine, diethylamine, dipropylamine and diisopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Aryl groups include phenyl, naphthyl, biphenyl, phenanthrenyl, naphthacenyl, and the like (see e.g. *Lang's Handbook of Chemistry* (Dean, J. A., ed) $13^{th}$ ed. Table 7-2 [1985]). In a particular embodiment aryl may be phenyl. Substituted phenyl or substituted aryl denotes a phenyl group or aryl group substituted with one, two, three, four or five, such as 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or more methyne (CH) and/or methylene ($CH_2$) groups in these substituents may in turn be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Substituted phenyl groups include 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any (for example 1, 2 or 3) of the substituents specified herein in the same manner as substituted alkyl groups.

"Carbocyclyl", "carbocyclylic", "carbocycle" and "carbocyclo" alone and when used as a moiety in a complex group such as a carbocycloalkyl group, refers to a mono-, bi-, or tricyclic aliphatic ring having 3 to 14 carbon atoms, for example 3 to 7 carbon atoms, which may be saturated or unsaturated, aromatic or non-aromatic and may be bridged. Saturated carbocyclic groups include cyclopropyl, cyclobutyl, cyclopentyl and cyclohexyl groups. In a particular embodiment carbocycle groups are cyclopropyl and cyclohexyl. In another particular embodiment carbocycle group is cyclohexyl. Unsaturated carbocycles include aromatic e.g. aryl groups as previously defined for example phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Carboxylic acid protecting groups include allyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" denotes the group —NH—C(NH)—NHR wherein R is H or alkyl or aralkyl. A particular guanidine group is —NH—C(NH)—$NH_2$.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, for example from 5 to 14 ring atoms, where the ring atoms are carbon and at least one heteroatom (nitrogen, sulfur or oxygen), for example 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Non-aromatic heterocycles include morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. 5-membered heterocycles containing a sulfur or oxygen atom and one to three nitrogen atoms include thiazolyl, for example thiazol-2-yl and thiazol-2-yl N-oxide, thiadiazolyl, for example 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. 5-membered ring heterocycles containing 2 to 4 nitrogen atoms include imidazolyl, for example imidazol-2-yl; triazolyl, for example 1,3,4-triazol-5-yl; 1,2,3-triazol-5-yl, 1,2,4-triazol-5-yl, and tetrazolyl, for example 1H-tetrazol-5-yl. Benzo-fused 5-membered heterocycles include benzoxazol-2-yl, benzthiazol-2-yl and benzimidazol-2-yl. 6-membered heterocycles containing one to three nitrogen atoms and optionally a sulfur or oxygen atom include pyridyl, such as pyrid-2-yl, pyrid-3-yl, and pyrid-4-yl; pyrimidyl, for example pyrimid-2-yl and pyrimid-4-yl; triazinyl, for example 1,3,4-triazin-2-yl and 1,3,5-triazin-4-yl; pyridazinyl, for example pyridazin-3-yl, and pyrazinyl. In a particular embodiment 6-membered heterocycles include pyridine N-oxides and pyridazine N-oxides and the pyridyl, pyrimid-2-yl, pyrimid-4-yl, pyridazinyl and the 1,3,4-triazin-2-yl groups. Substituents for optionally substituted heterocycles, and further examples of the 5- and 6-membered ring systems discussed above can be found in W. Druckheimer et al., U.S. Pat. No. 4,278,793.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from nitrogen, oxygen, and sulfur. In a particular embodiment, heteroaryl groups contain at least one heteroatom (*Lang's Handbook of Chemistry*, supra). Included in the definition are bicyclic groups where any of the above heteroaryl rings are fused to a benzene ring. In a particular embodiment, heteroaryls incorporate at least one nitrogen and/or oxygen heteroatom. The following ring systems are examples of the heteroaryl (which may be substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. In a particular embodiment, "heteroaryl" includes 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and S-aminotetrazolo[1,5-b]-pyridazin-6-yl. Alternatively, "heteroaryl" groups include 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, acetoxy, carbamoyloxy, trifluoro, chloro, carboxy, bromo and iodo groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with a hydroxy-protecting group such as those described above.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular salts are ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. In a particular embodiment, organic non-toxic bases are isopropylamine, diethylamine, ethanolamine, trimethamine, dicyclohexylamine, choline, and caffeine.

The phrase "and salts and solvates thereof" as used herein means that compounds of the inventions may exist in one or more salt or solvate forms. For example a compound of the invention may be substantially pure in one particular salt or solvate form or else may be mixtures of two or more salt or solvate forms.

The present invention provides novel compounds having the general formula I:

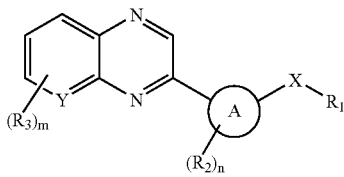

wherein A, X, Y, $R_1$, $R_2$, and $R_3$ are as defined herein.

A is a carbocycle or heterocycle ring substituted with 0 to 3 (e.g. n is 0-3) $R_2$ groups selected from the group consisting of halogen, hydroxyl, alkyl, acyl or alkoxy each optionally substituted with hydroxyl, halogen, amino, nitro, alkyl, acyl, alkylsulfonyl or alkoxy. In a particular embodiment, A is optionally substituted aryl or heteroaryl. In particular embodiment A is optionally substituted benzene, thiophene, thiazole, imidazole, pyrrole, N-alkyl pyrrole, pyrazole or N-alkyl pyrazole. In a particular embodiment A is a ring selected from the group consisting of $A^1$ and $A^2$:

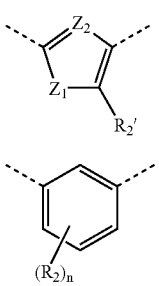

wherein $Z_1$ is O, S or $NR_5$ wherein $R_5$ is H or alkyl; $Z_2$ is CH, $CR_2$ or N; $R_2$ is halogen, hydroxyl, alkyl, acyl or alkoxy each optionally substituted with hydroxyl, halogen, amino, nitro, alkyl, acyl, alkylsulfonyl or alkoxy; $R_2$ is H, halogen, hydroxyl, alkyl, acyl or alkoxy each optionally substituted with hydroxyl, halogen, amino, nitro, alkyl, acyl, alkylsulfonyl or alkoxy; and n is 0-3. In a particular embodiment A is the ring of formula $A^1$. In a particular embodiment, A is the ring $A^1$ wherein $Z_1$ is S and $Z_2$ is CH or N. In another embodiment, $Z_1$ is S and $Z_2$ is CH, i.e. thiophene. In another embodiment $Z_1$ is S and $Z_2$ is N, i.e. thiazole. In particular embodiment $R_{2'}$ is H. In particular embodiment $R_{2'}$ is methyl. In another particular embodiment A is the ring of formula $A^2$. In a particular embodiment $R_{2'}$ is methyl. In a particular embodiment A is ring $A_2$. In such embodiment $R_2$ may be absent, i.e. n is 0. In another embodiment, n is 1 and $R_2$ is Cl. In a particular embodiment A is the ring $A^{1a}$, $A^{1b}$ or $A^{2a}$:

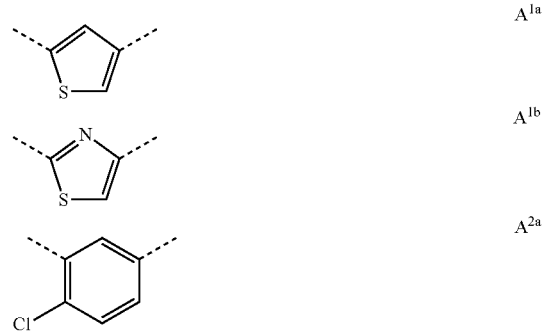

In a particular embodiment A is the ring of formula $A^{1a}$. In another embodiment A is the ring of formula $A^{1b}$. In another embodiment A is the ring of formula $A^{2a}$.

X is alkylene, $NR_4C(O)$, $NR_4C(S)$, $NR_4C(NH)$, $NR_4SO$, $NR_4SO_2$, $NR_4C(O)NH$, $NR_4C(S)NH$, $C(O)NR_4$, $C(S)NR_4$, $C(NH)NR_4$, $NR_4PO$ or $NR_4PO(OH)$ wherein $R_4$ is H or alkyl. Alternatively, X is alkylene, $NR_4C(O)$, $NR_4C(S)$, $NR_4SO$, $NR_4SO_2$, $NR_4C(O)NH$, $NR_4C(S)NH$, $C(O)NR_4$, $C(S)NR_4$, $NR_4PO$ or $NR_4PO(OH)$ wherein $R_4$ is H or alkyl. In a particular embodiment X is $NR_4C(O)$ which forms an amide linkage between ring A and $R_1$. In a particular embodiment X is $NR_4C(NH)$ which forms an amidine linkage between ring A and $R_1$. In another embodiment, X is $NR_4C(S)$, which forms a thioamide linkage between ring A and $R_1$. In another embodiment, X is $NR_4C(O)NH$ which forms a urea linkage between ring A and $R_1$. In another embodiment X is $NR_4C(S)NH$ which with $NR_2$ forms a thiourea linkage between ring A and $R_1$.

Y is N, CH or $CR_3$. In a particular embodiment Y is CH or $CR_3$. In another embodiment Y is CH. In another embodiment Y is N.

$R_1$ is selected from the group consisting of alkyl, cycloalkyl, aryl or a heterocycle each of which is optionally substituted with hydroxyl, halogen, amino, nitro, alkyl, acyl, alkylsulfonyl, haloalkyl or alkoxy; and said cycloalkyl, aryl and heterocycle are optionally further substituted with —$(CH_2)_s$-$(Q)_u$-$(CH_2)_t$-Z wherein Q is C(O), S(O), $SO_2$, C(O)O, OC(O), $NR_4C(O)$, $NR_4C(S)$, $NR_4SO$, $NR_4SO_2$, $NR_4C(O)NH$, $NR_4C(S)NH$, $C(O)NR_4$, or $C(S)NR_4$; and Z is hydroxyl, amino, halogen, alkylsulfonly, alkoxy, alkoxycarbonyl, haloalkyl, a carbocycle, a heterocycle or a carbocycle or heterocycle substituted with hydroxyl, halogen, amino, nitro, alkyl, acyl, alkylsulfonyl, haloalkyl, hydroxyalkyl, alkoxy or alkoxyalkoxy; and s and t are independently 0 to 5 and u is 0 or 1. Alternatively, $R_1$ is selected from the group consisting of cycloalkyl, aryl or a heterocycle each of which is optionally substituted with hydroxyl, halogen, amino, nitro, alkyl, acyl, alkylsulfonyl or alkoxy.

In a particular embodiment $R_1$ is a cycloalkyl, aryl or heterocycle optionally substituted with hydroxyl, halogen, amino, nitro, alkyl, acyl, alkylsulfonyl, haloalkyl or alkoxy; and said cycloalkyl, aryl and heterocycle is further substituted with —$(CH_2)_s$-$(Q)_u$-$(CH_2)_t$-Z wherein Q is C(O), S(O), $SO_2$, C(O)O, OC(O), $NR_4C(O)$, $NR_4C(S)$, $NR_4SO$, $NR_4SO_2$, $NR_4C(O)NH$, $NR_4C(S)NH$, $C(O)NR_4$, or $C(S)NR_4$; and Z is hydroxyl, amino, halogen, alkylsulfonly, alkoxy, alkoxycarbonyl, haloalkyl, a carbocycle, a heterocycle or a carbocycle or heterocycle substituted with hydroxyl, halogen, amino, nitro, alkyl, acyl, alkylsulfonyl, haloalkyl, hydroxyalkyl, alkoxy or alkoxyalkoxy; and s and t are independently 0 to 5 and u is 0 or 1.

In a particular embodiment Q is C(O). In another embodiment Q is C(O)NH. In another embodiment Q is C(O)O. In another embodiment Q is SO$_2$. In another embodiment Q is SO$_2$NH. In another embodiment Q is NH. In an embodiment s is 0. In another embodiment s is 0 to 3. In an embodiment t is 0. In another embodiment t is 0 to 3. In an embodiment u is 0. In another embodiment u is 1.

In particular embodiment Z is a carbocycle or heterocycle selected from the group consisting of piperidine, piperazine, pyrrolidine, morpholino, pyrazole, triazole, pyrrolidone, imidazole and thiomorpholine. In a particular embodiment Z is a carbocycle or heterocycle selected from the group consisting of piperidin-1-yl, 4-hydroxy-piperidin-1-yl, N-methyl-piperidin-4-yl, piperazin-1-yl, N-methyl-piperazin-1-yl, N-ethyl-piperazin-1-yl, N-acetyl-piperazin-1-yl, pyrrolidin-1-yl, 3,5-dimethyl-piperazin-1-yl, morpholin-1-yl, thiomorpholin-1-yl, 3,5-dimethyl-morpholin-1-yl, N-hydroxyethyl-piperazin-1-yl, pyrazol-1-yl, 1,2,4-triazol-1-yl, pyrrolid-2-one-1-yl and imidazol-5-yl. In another particular embodiment Z is hydroxy, dimethylamino, CF$_3$, methoxycarbonyl or methoxy.

Alternatively, R$_1$ is selected from the group consisting of cycloalkyl, aryl or a heterocycle each of which is optionally substituted with hydroxyl, halogen, amino, nitro, alkyl, acyl, alkylsulfonyl or alkoxy. In a particular embodiment R$_1$ is optionally substituted aryl or heteroaryl. In a particular embodiment R$_1$ is an optionally substituted phenyl group. In another particular embodiment R$_1$ is an optionally substituted pyridine group. In a particular embodiment R$_1$ is of formula IIa, IIb, IIc, IId, IIe, IIf, IIg, IIh, IIi, IIj, IIk, IIl or IIm:

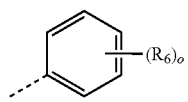

IIa

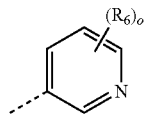

IIb

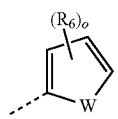

IIc

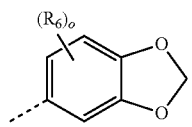

IId

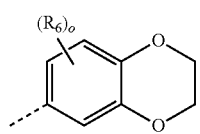

IIe

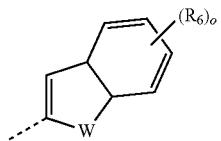

IIf

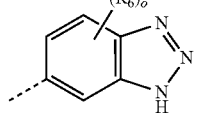

IIg

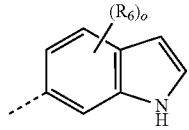

IIh

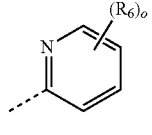

IIi

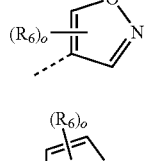

IIj

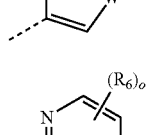

IIk

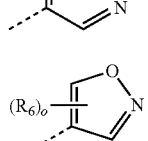

IIl

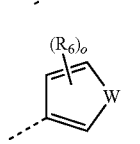

IIj

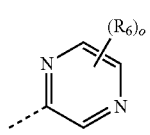

IIk

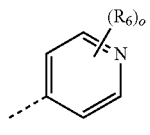

IIl

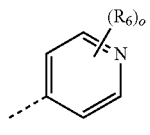

IIm wherein W is O, S or NR$_7$ wherein R$_7$ is H or alkyl; R$_6$ is halogen, amino, nitro, alkyl, acyl, alkylsulfonyl or alkoxy; and o is 0-3. In a particular embodiment W is S. In a particular embodiment R$_1$ is the group of formula IIa. In such embodiment R$_6$ may be alkoxy and o is 1, 2 or 3. Particular IIa groups are IIa$^1$-IIa$^{28}$:

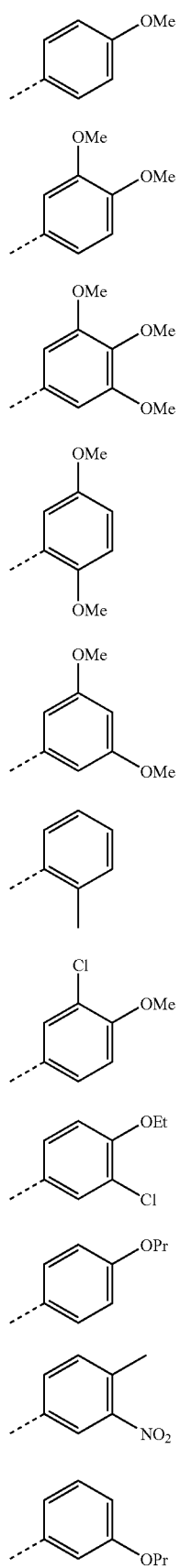
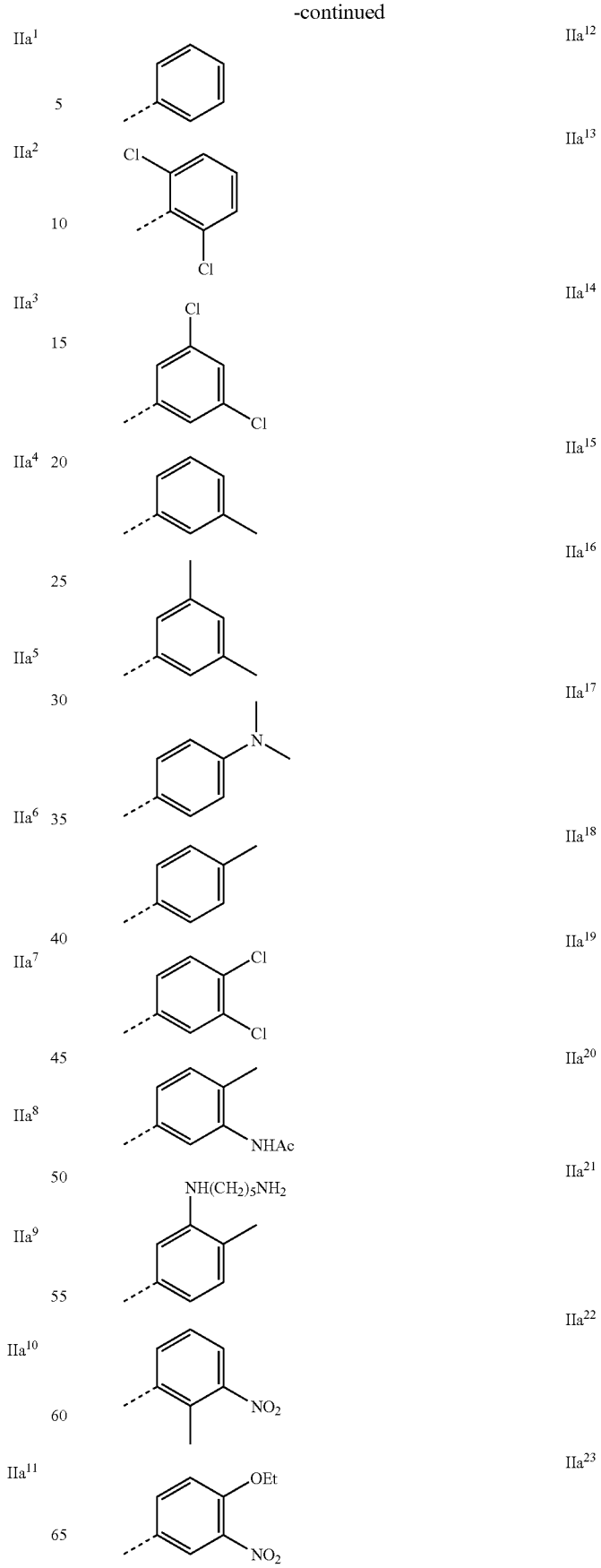

-continued

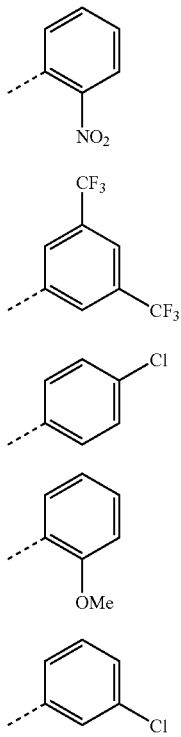

IIa²⁴

IIa²⁵

IIa²⁶

IIa²⁷

IIa²⁸

In another particular embodiment R₁ is the group of formula IIb. In such embodiment R₆ may be alkyl or haloalkyl (e.g. CF₃). Particular IIb groups are IIb¹-IIb³:

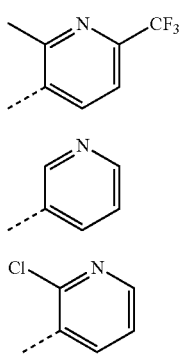

IIb¹

IIb²

IIb³

In a particular embodiment R₁ is the group of formula IIc. In such embodiment W may be S and o is 0. In another particular embodiment R₁ is the group of formula IId. In such embodiment o may be 0. In another particular embodiment R₁ is the group of formula IIe. In such embodiment o may be 0. In another particular embodiment R₁ is the group of formula IIf. In such embodiment o may be 0.

R₂ is halogen, hydroxyl, alkyl, acyl or alkoxy each optionally substituted with hydroxyl, halogen, amino, nitro, alkyl, acyl, alkylsulfonyl or alkoxy. n is 0-3, for example 0 or 1. In a particular embodiment R₂ is hydroxyl. In a particular embodiment R₂ is alkyl or alkyl substituted with halogen, methyl or trifluoromethyl. In a particular embodiment R₂ is acyl, for example alkanoyl e.g. acetyl. In a particular embodiment R₂ is halogen, for example Cl or F. In another particular embodiment R₂ is alkoxy, for example methoxy or ethoxy.

R₃ is halogen, hydroxyl, alkyl, haloalkyl, acyl or alkoxy; and m is 0-3. In a particular embodiment m is 0, i.e. R₃ is absent. In another particular embodiment m is 1-3 and R₃ is halogen (e.g. F) or alkyl (e.g. methyl).

Particular compounds of the invention include, but are not limited to the following:

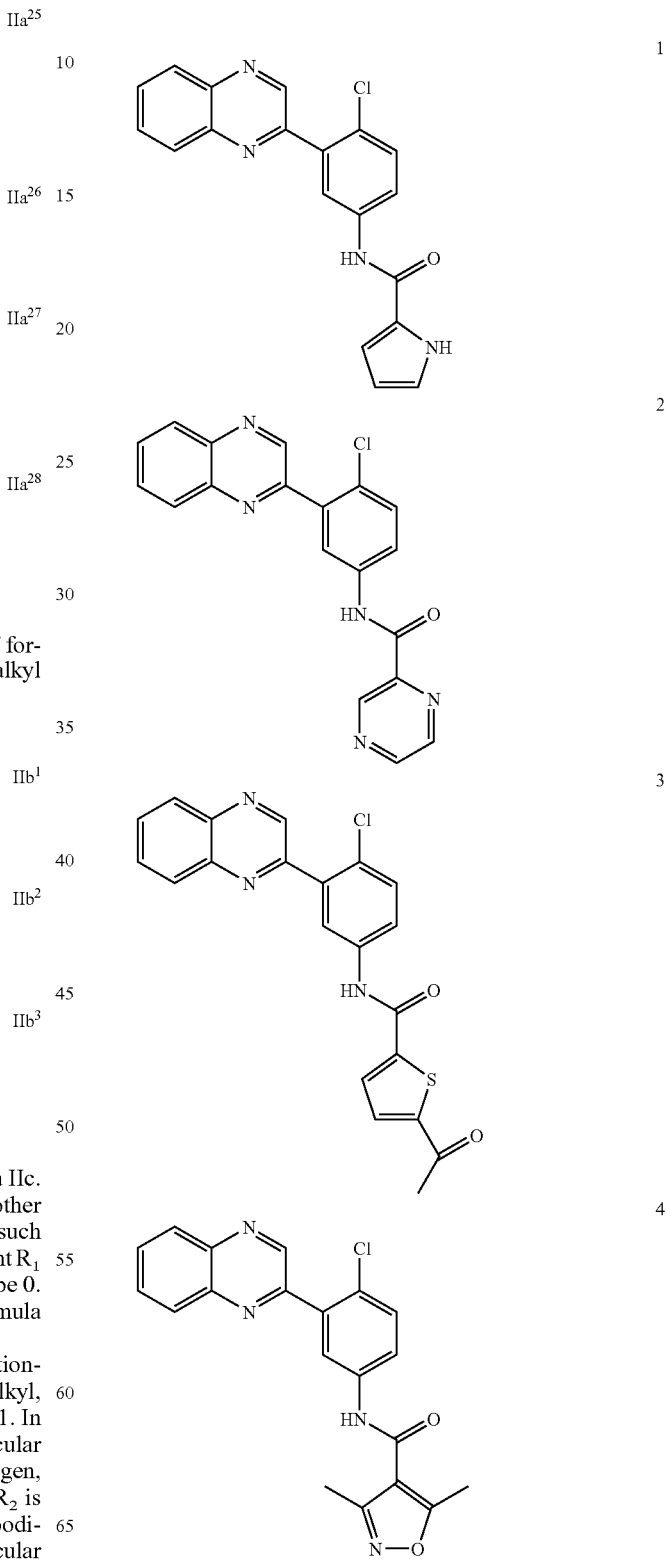

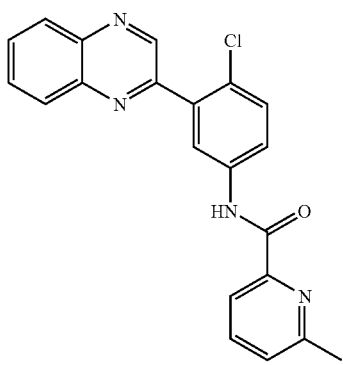
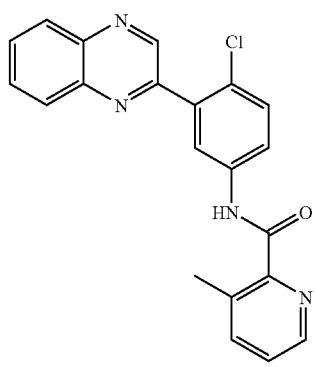
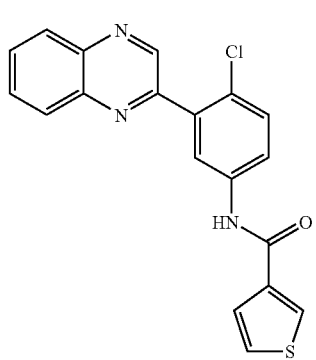
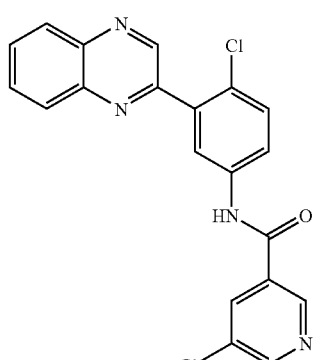
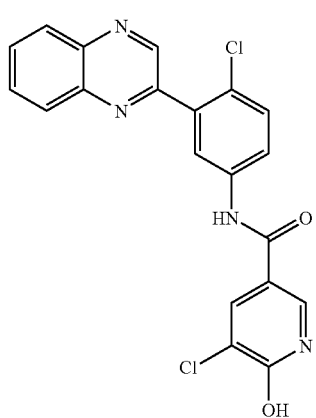

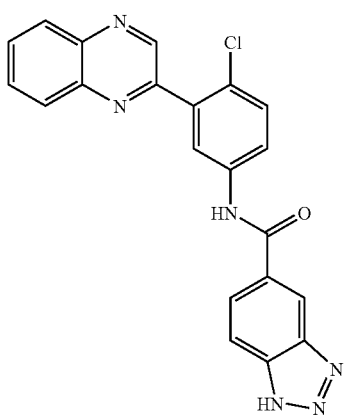
13
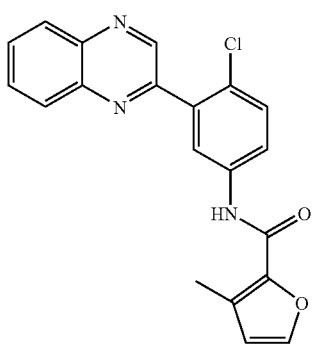
14
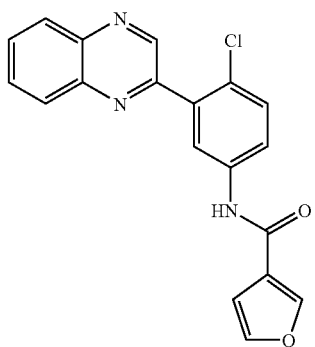
15
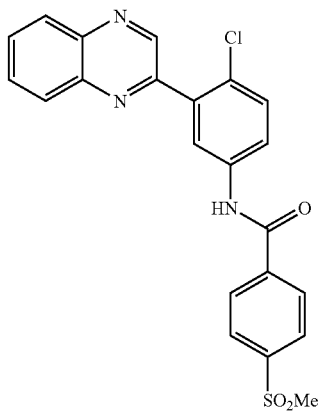
16
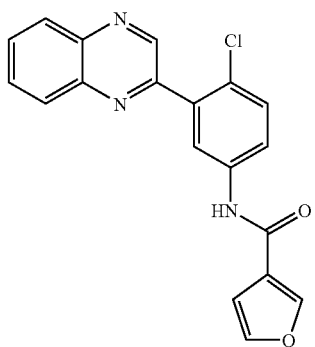
17
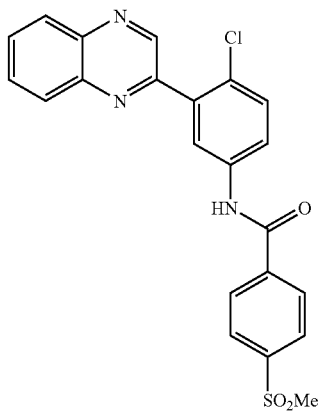
18
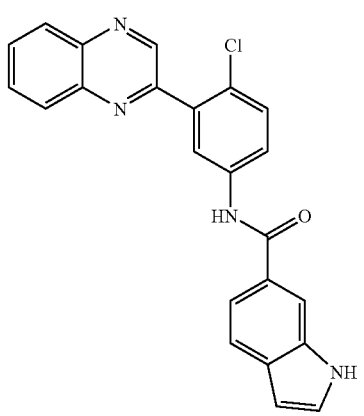
19
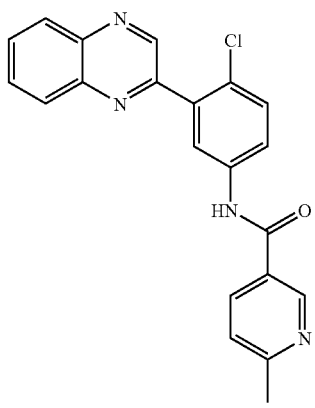
20

21
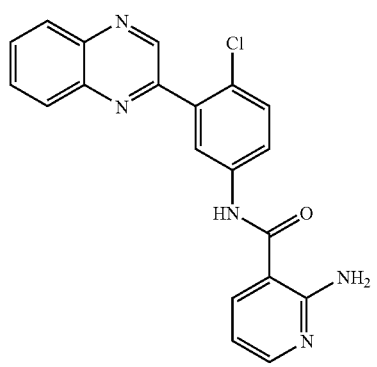
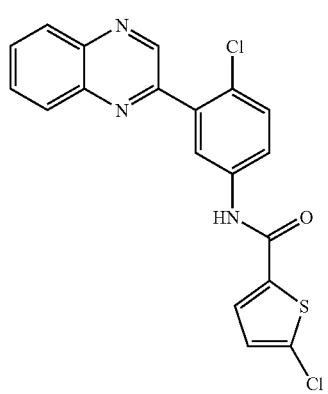
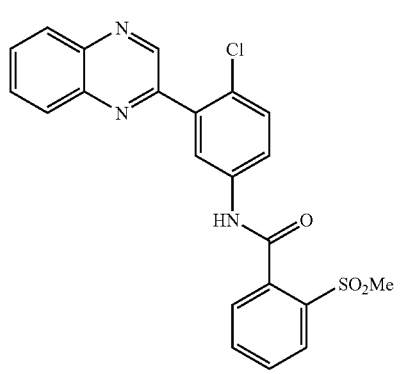
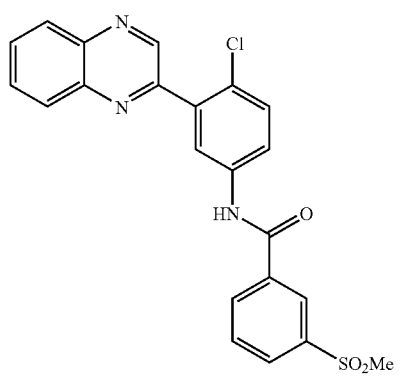
22
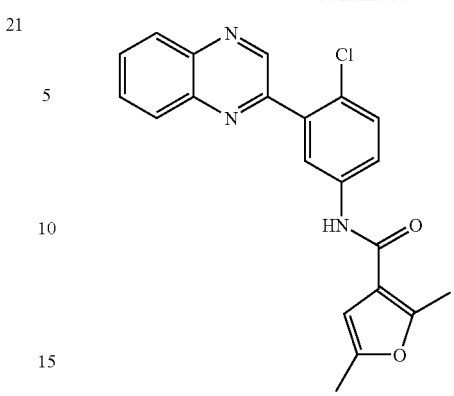
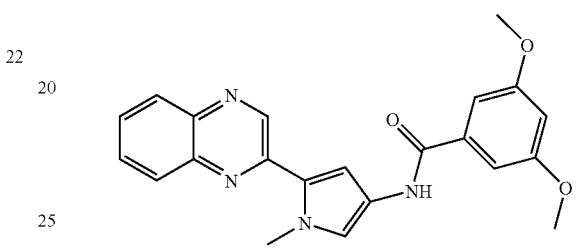
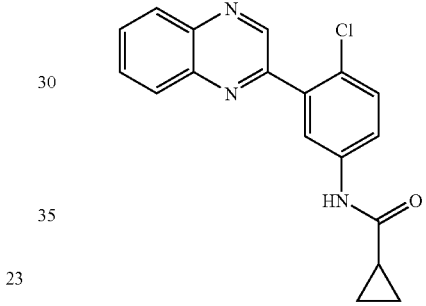
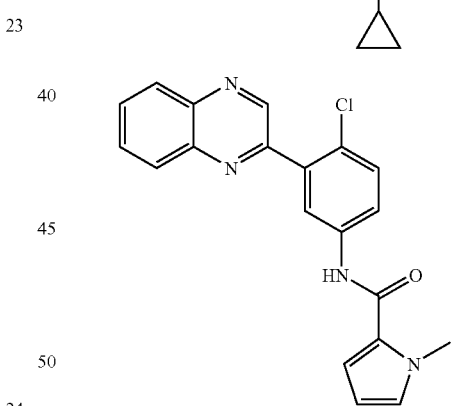
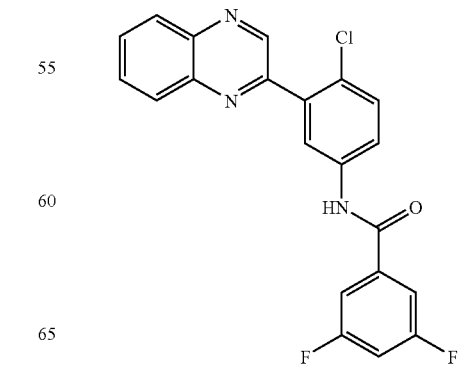

-continued
30
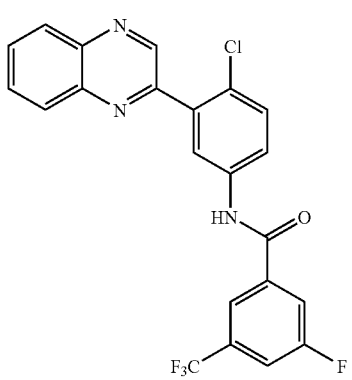
31
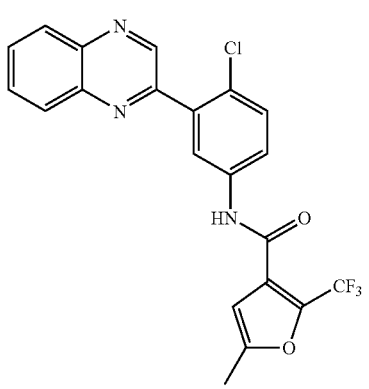
32
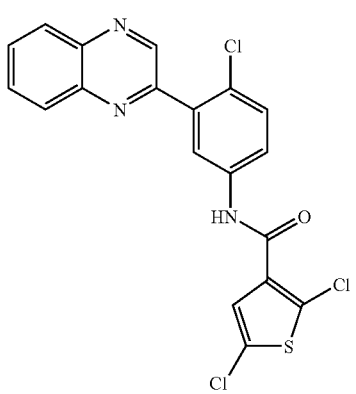
33
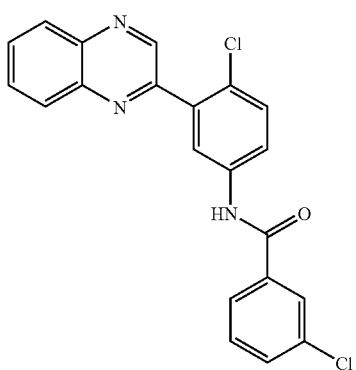
-continued
34
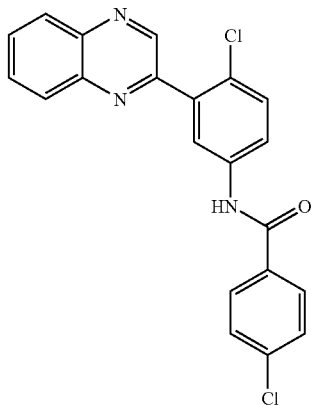
35
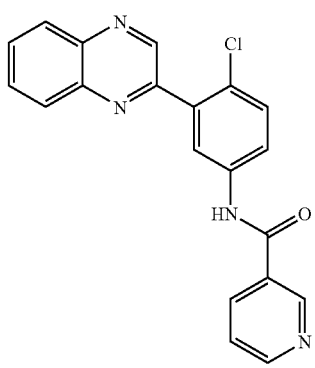
36
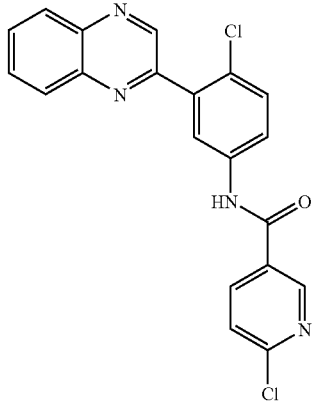
37
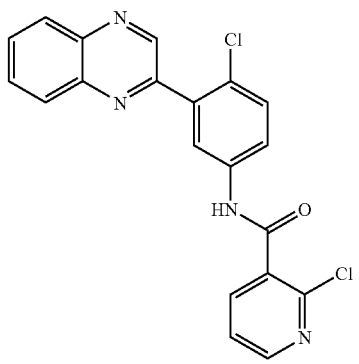

-continued
38
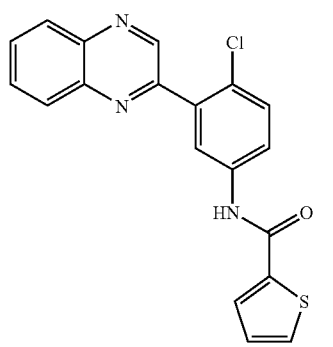
39
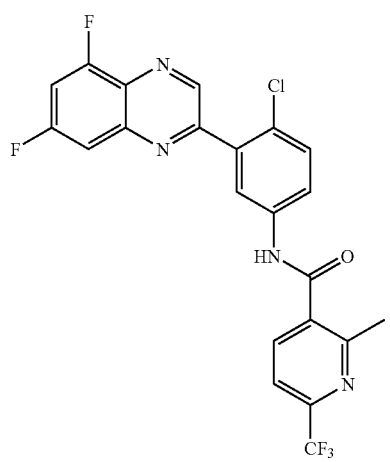
40
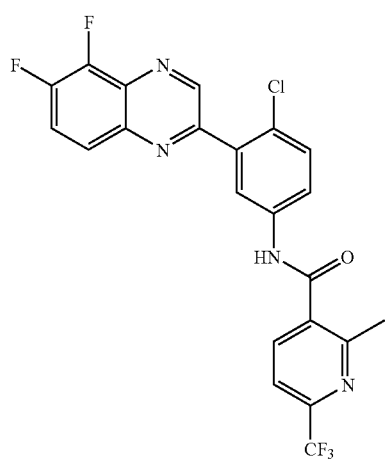
41
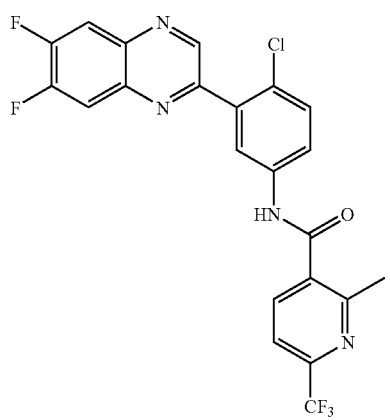
-continued
42
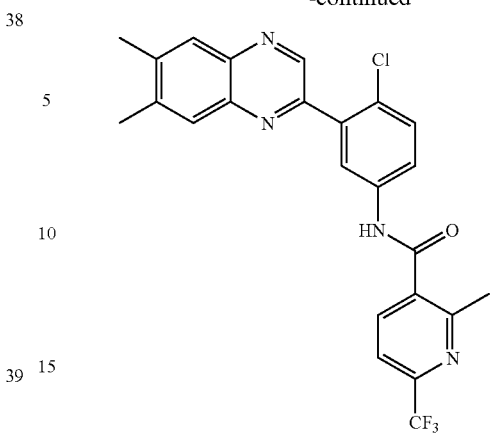
43
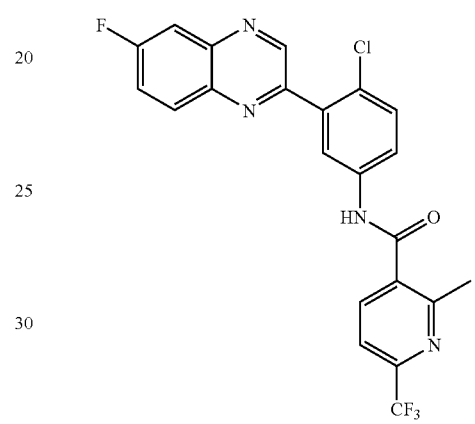
44
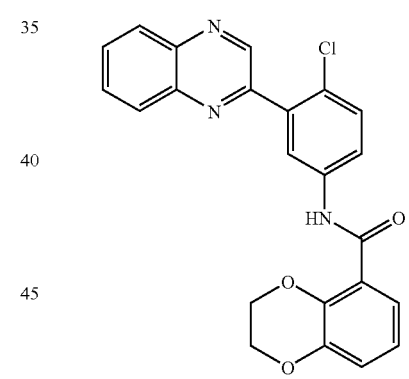
45
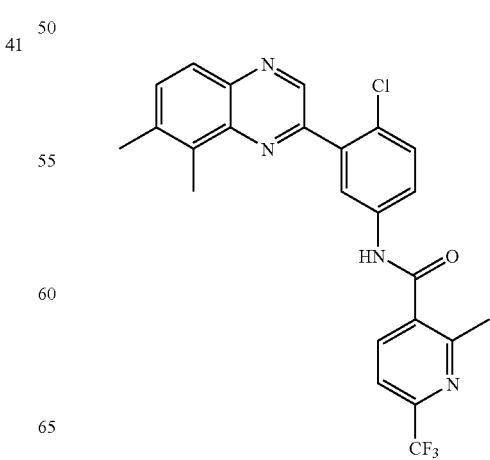

-continued
46
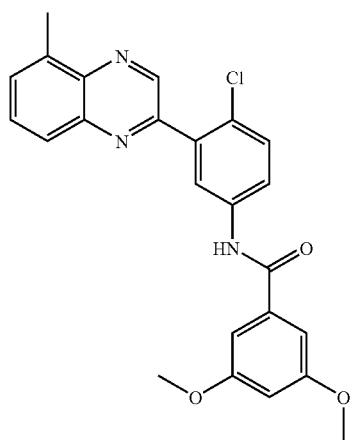
47
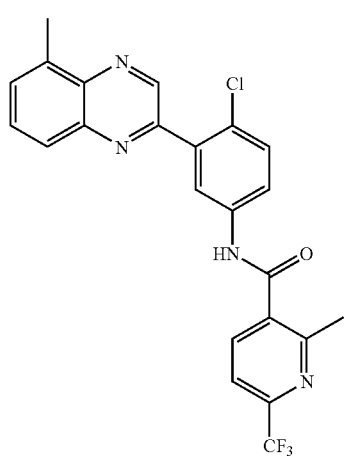
48
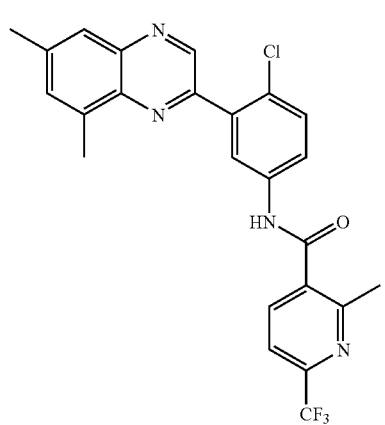
-continued
49
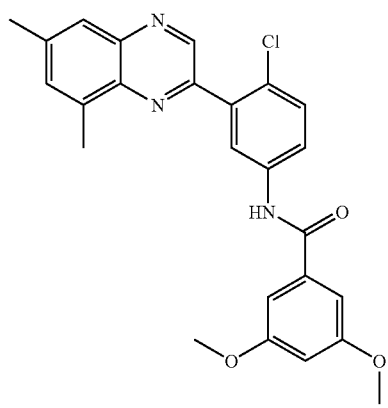
50
51
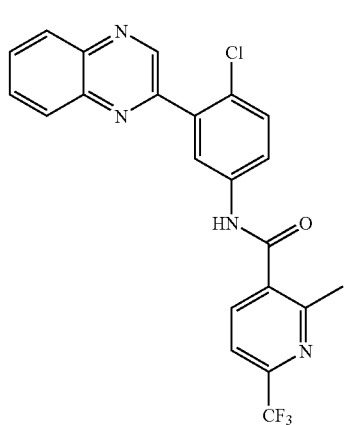
52

53
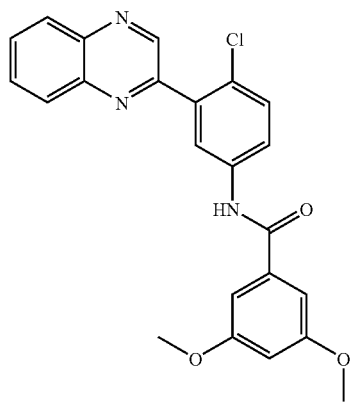
54
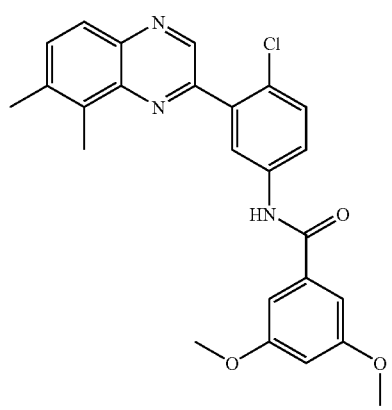
55
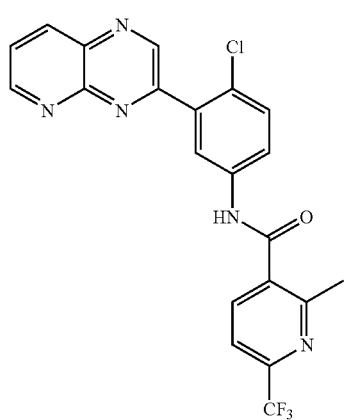
56
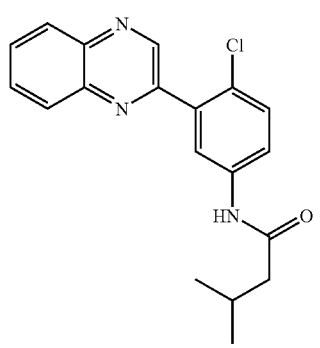
57
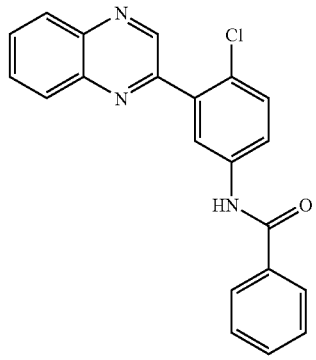
58
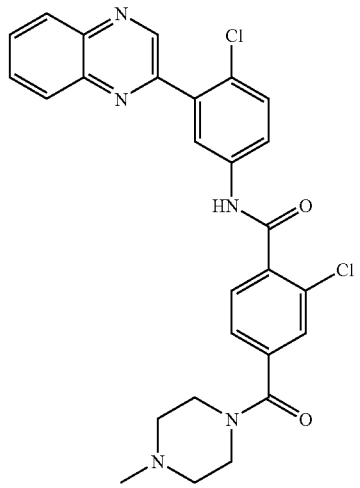
59
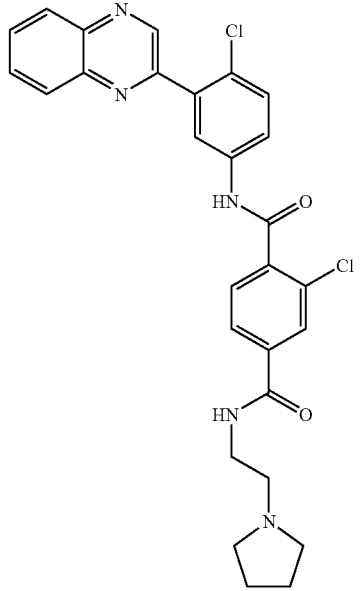

-continued
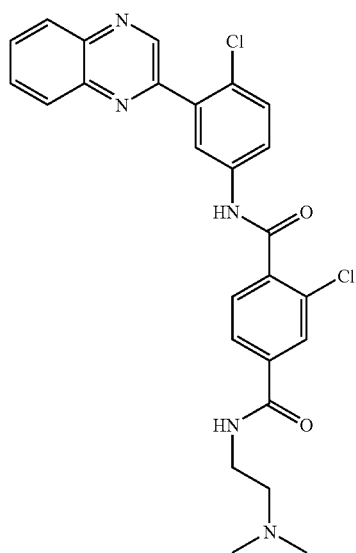
60
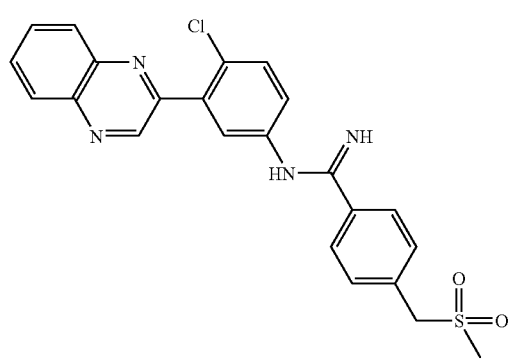
61
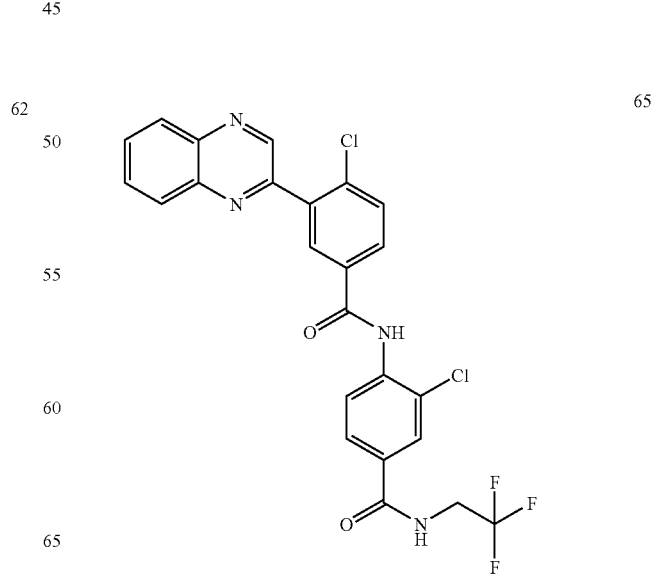
62
-continued
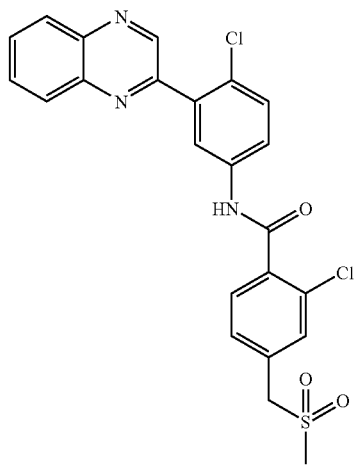
63
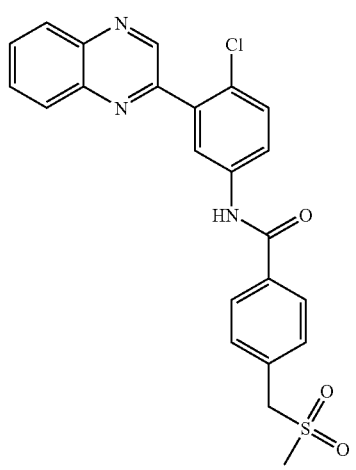
64
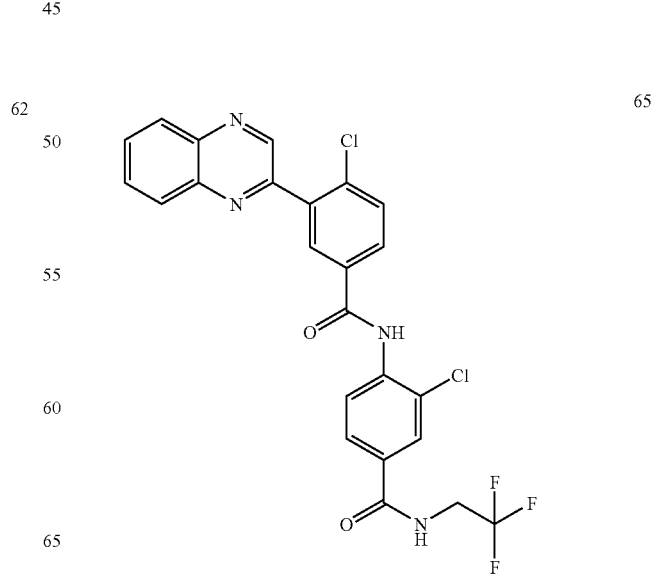
65

-continued
| | |
|---|---|
| 66 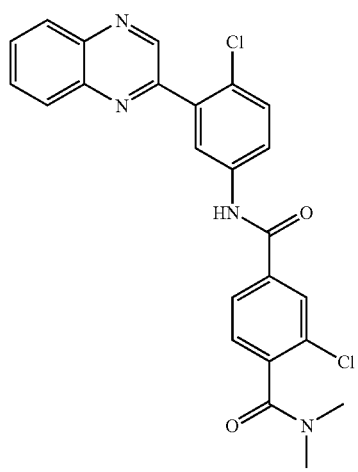 | 69 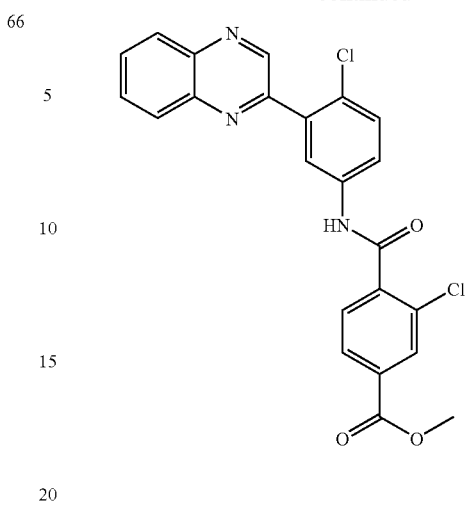 |
| 67 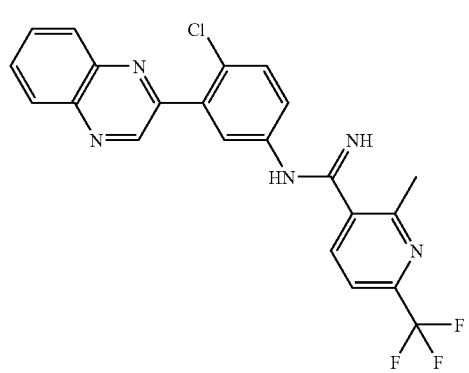 | 70 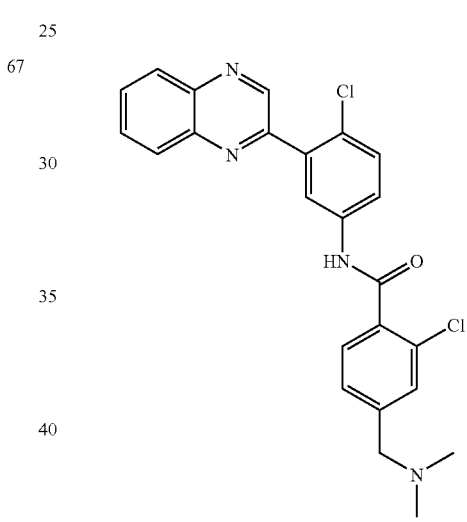 |
| 68 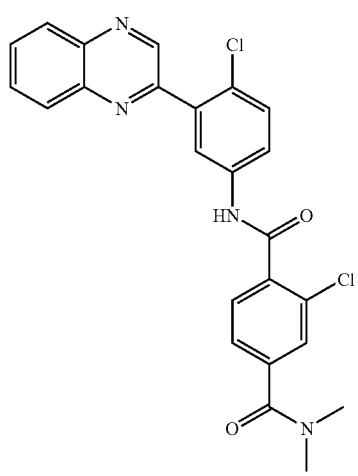 | 71 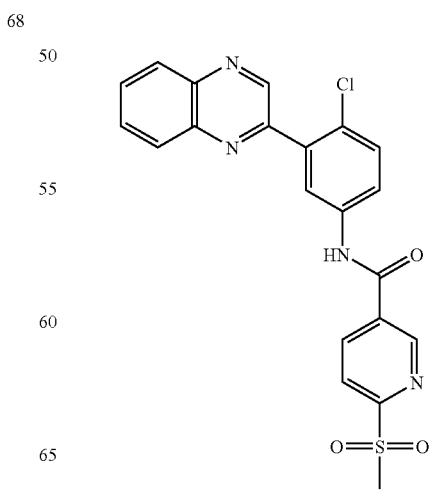 |

72
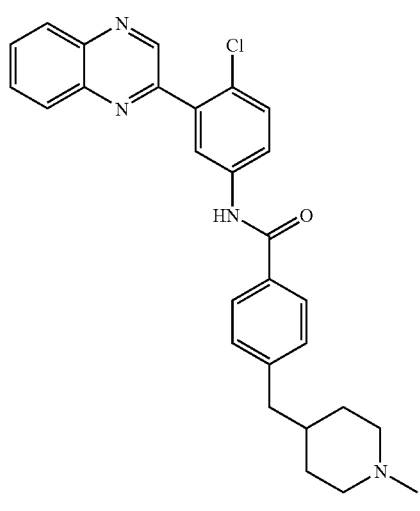
73
75
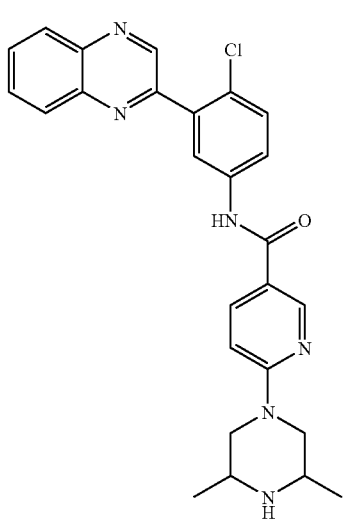
76
74
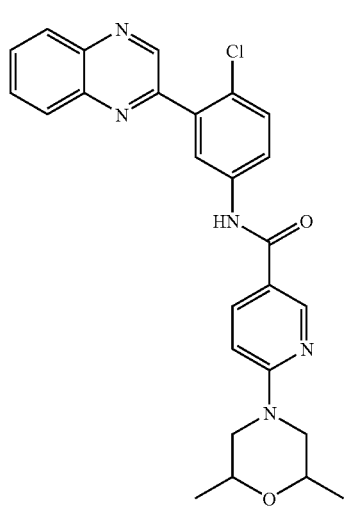
77
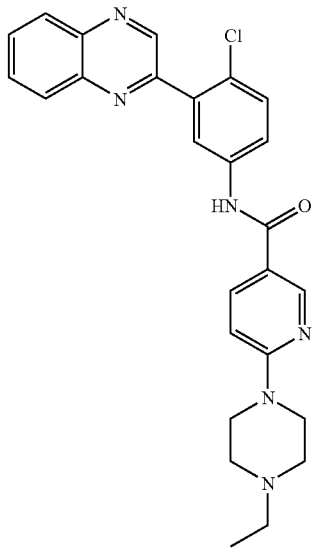

| 78 | 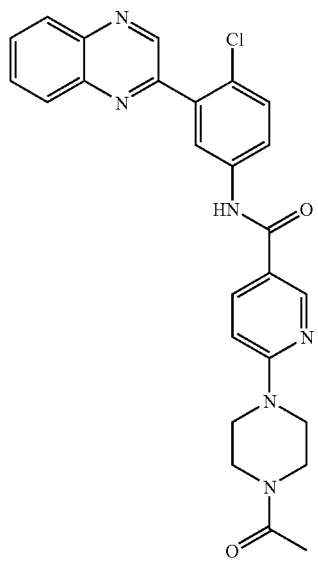 | 81 | 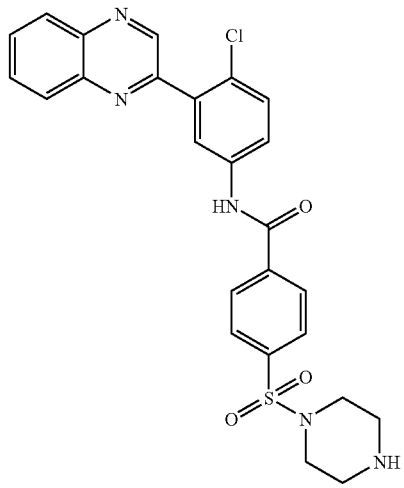 |
| 79 | 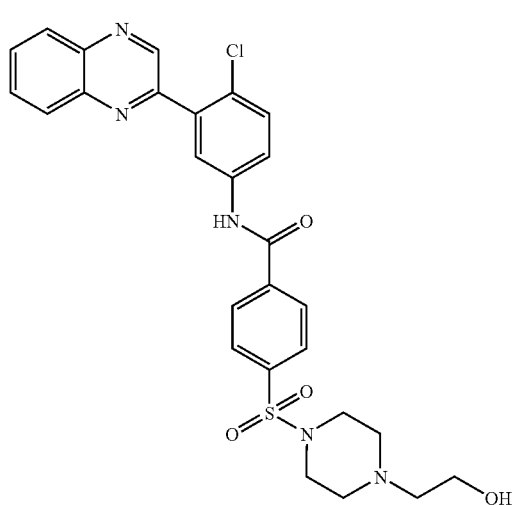 | 82 | 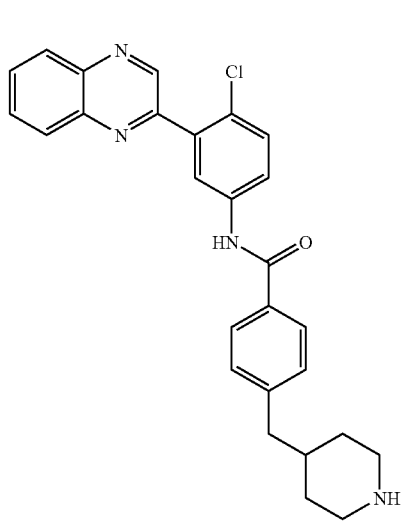 |
| 80 | 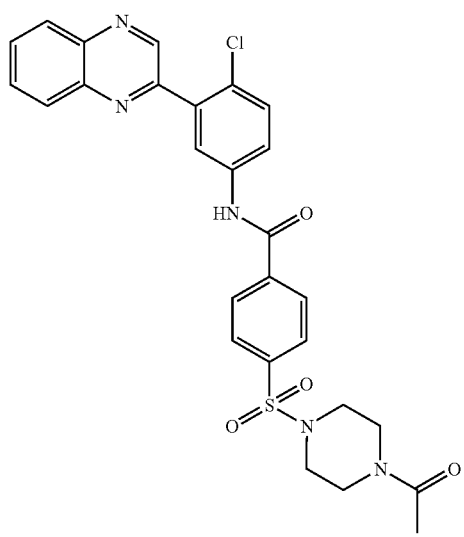 | 83 | 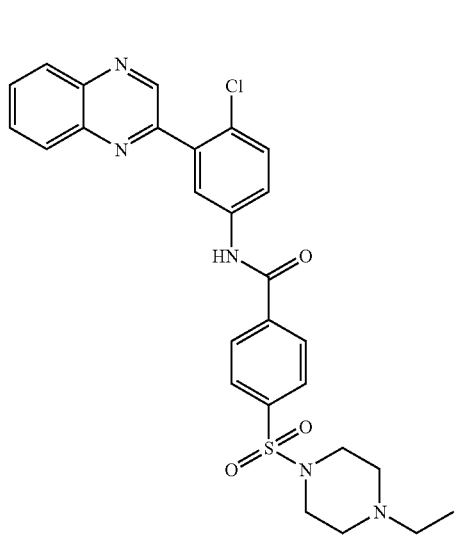 |

84
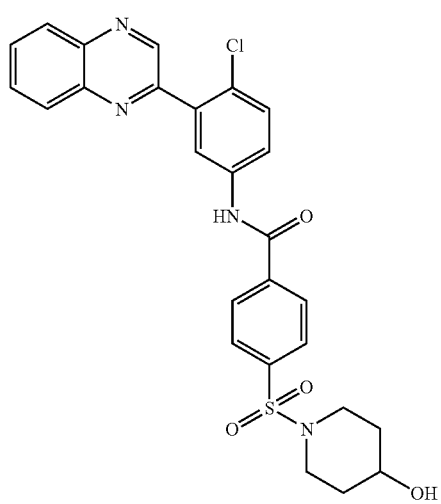
85
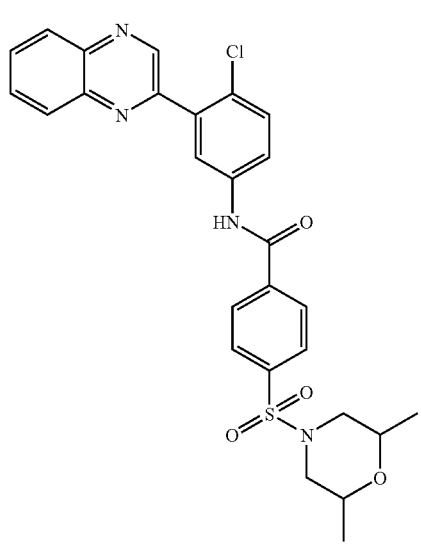
86
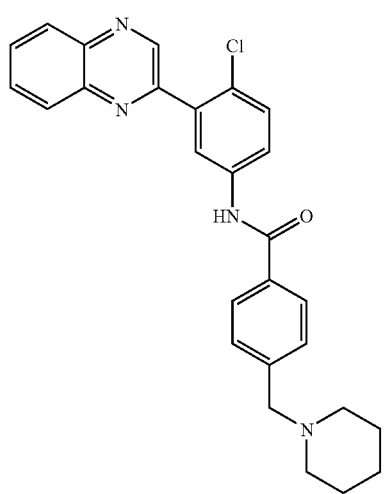
87
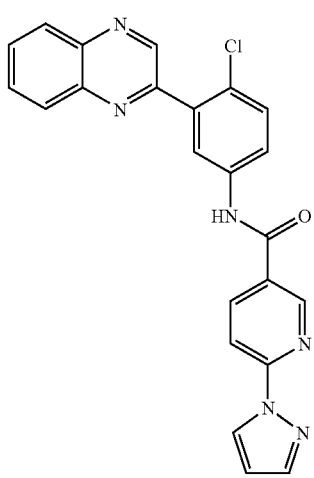
88
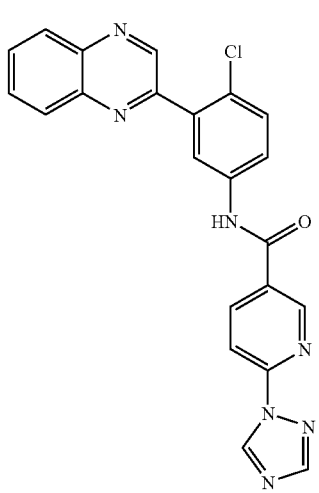
89
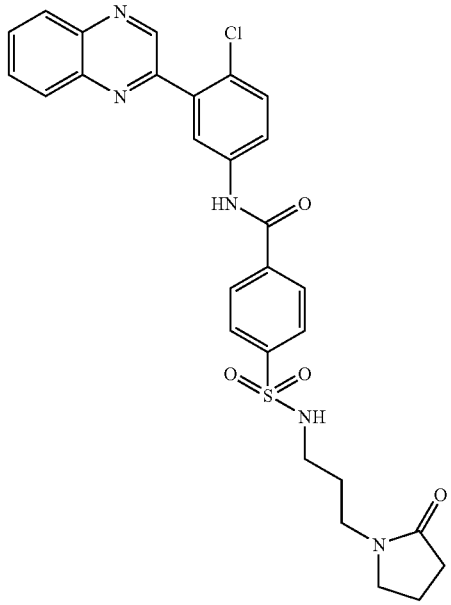

41
-continued
90
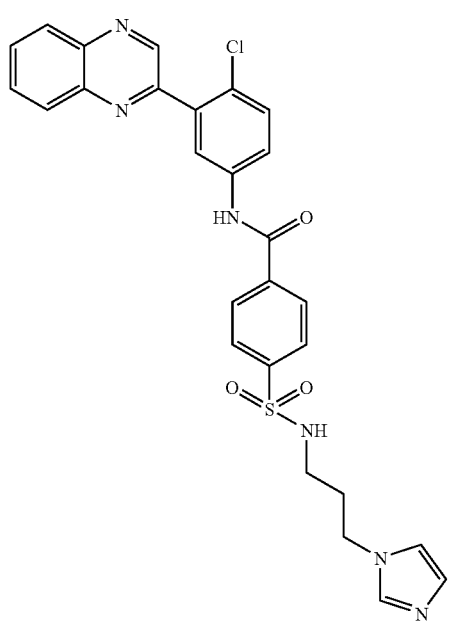
91
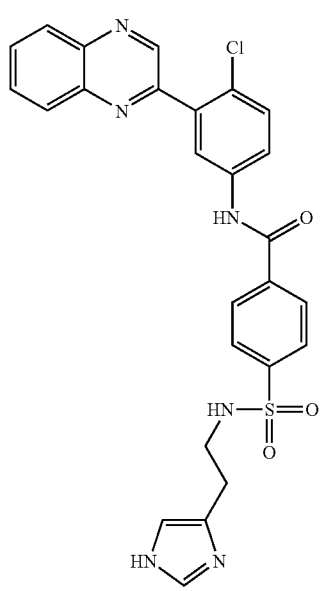
42
-continued
92
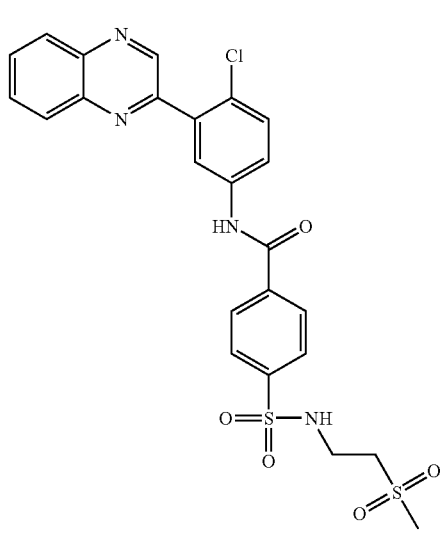
93
94
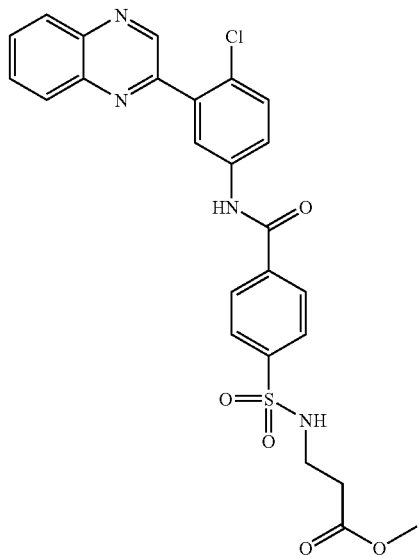

95
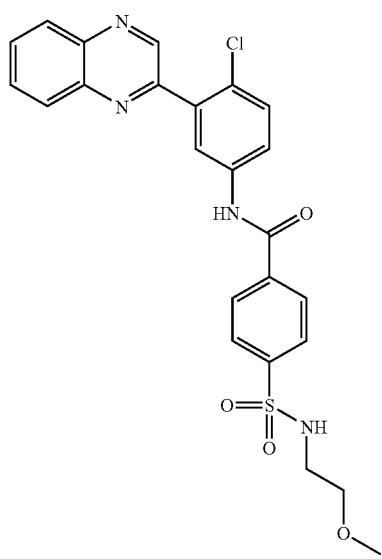
96
98
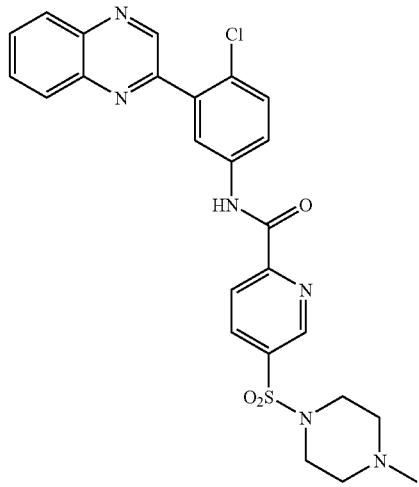
99
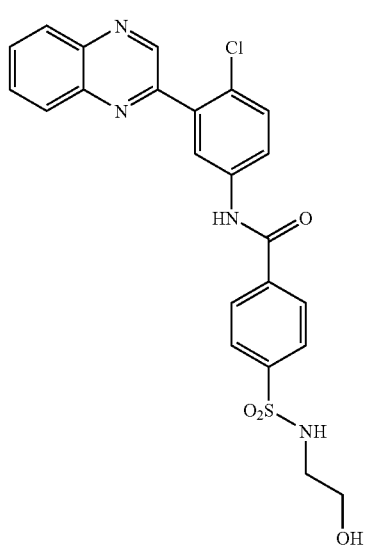
97
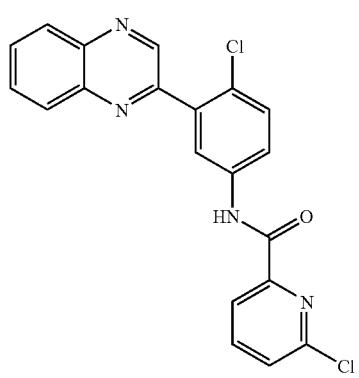
100
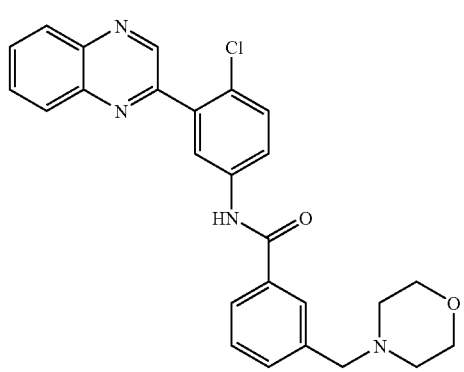

-continued
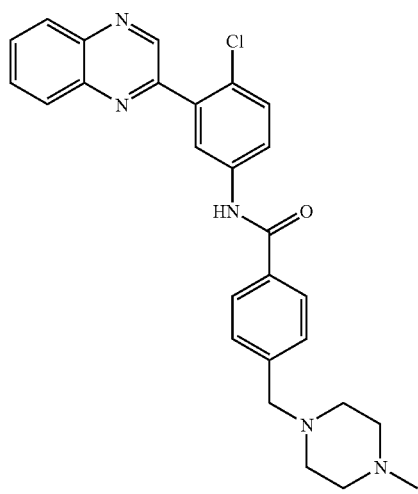
101
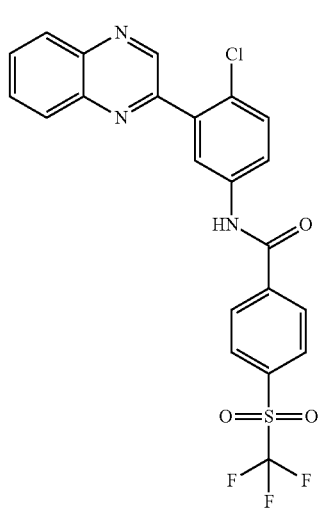
104
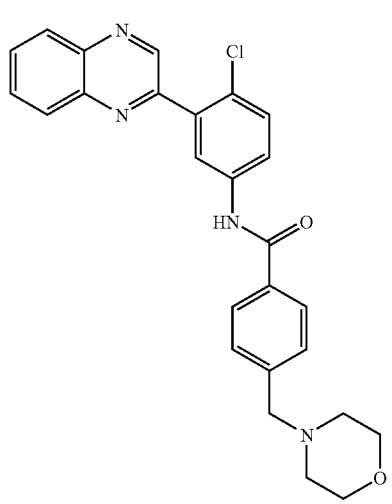
102
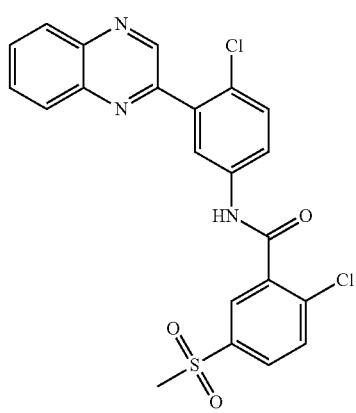
105
103
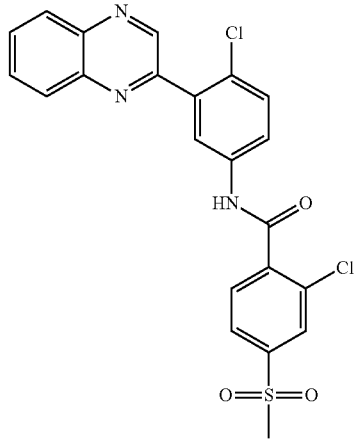
106

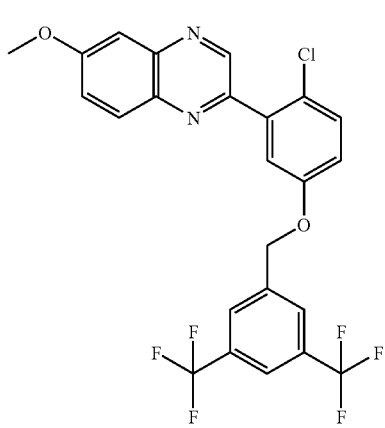
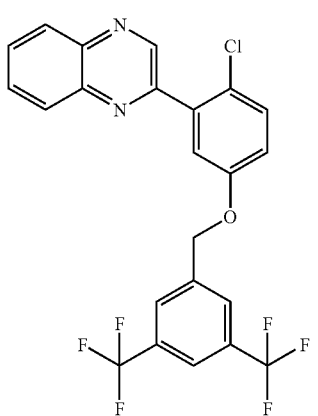
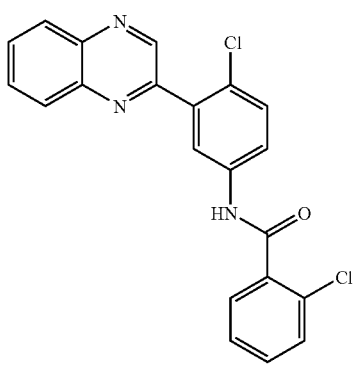
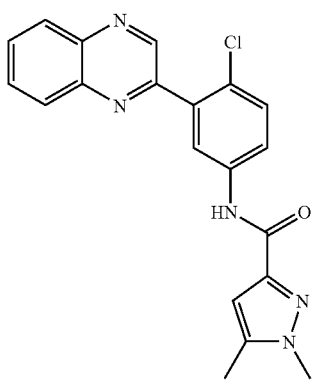
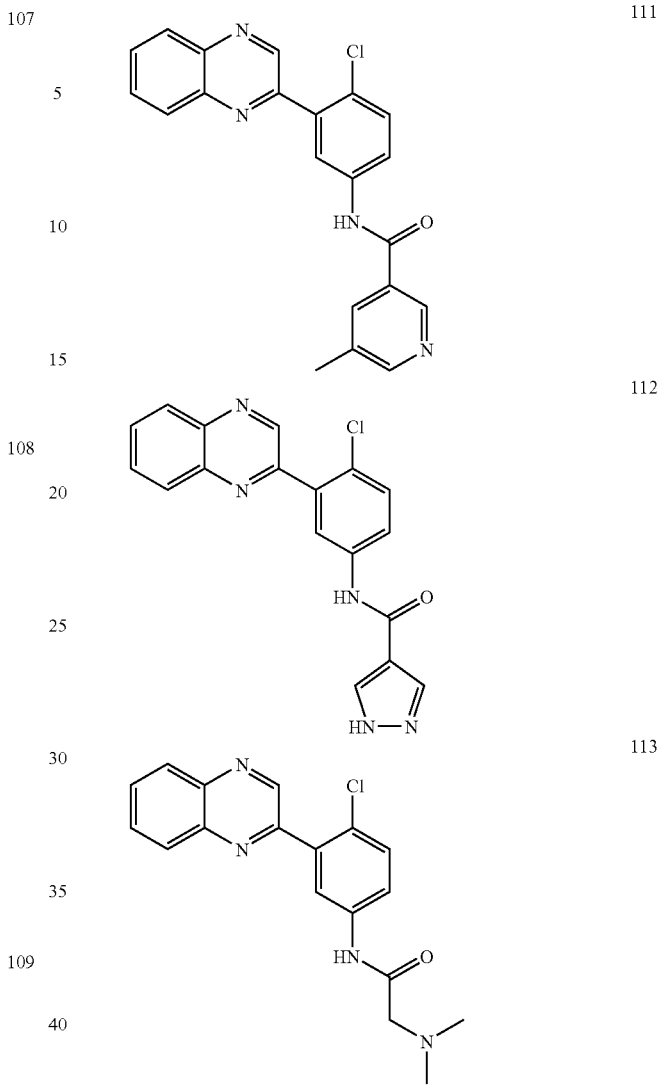

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

The invention also encompasses prodrugs of the compounds described above. Suitable prodrugs include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. Prodrug compounds may be prepared by reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50 C. The reactions are usually also carried out in the presence of an inorganic base such as potassium carbonate or sodium bicarbonate, or an organic base such as an amine, including pyridine, triethylamine, etc. One manner of preparing prodrugs is described in U.S. Ser. No. 08/843,369 filed Apr. 15, 1997 (corresponding to PCT publication WO9846576) the contents of which are incorporated herein by reference in their entirety.

Synthesis

Compounds of the invention are prepared using standard organic synthetic techniques from commercially available starting materials and reagents. It will be appreciated that synthetic procedures employed in the preparation of compounds of the invention will depend on the particular substituents present in a compound and that various, protection and deprotection procedures may be required as is standard in organic synthesis. Compounds of the invention in which X is NR$_4$C(O) may be prepared according to the general scheme 1.

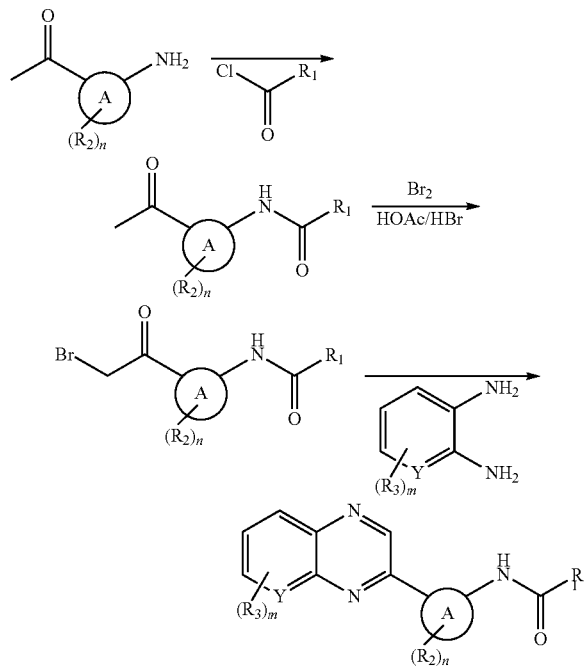

Scheme 1

Amine starting material is acylated by the appropriate acid chloride Cl—C(O)—R$_1$ and the resulting compound is then alpha-brominated with Br$_2$ in a mixture of acetic and hydrobromic acids. The alpha-bromo ketone intermediate is then converted to the final quinoxaline or 5-azaquinoxaline product by reacting with the appropriate 1,2-phenylenediamine or 2,3-pyridinediamine in the presence of a base such as sodium acetate. The same scheme may be used to prepare thioamide compounds of the invention, i.e. X is NR$_4$C(S), by employing an appropriate thio acid chloride Cl—C(S)—R$_1$ in the acylation step. Starting materials and reagents in this and subsequent synthetic schemes are either commercially available or may be prepared using commercially available starting materials using established organic chemistry technique.

Compounds of the invention in which X is NR$_4$C(O)NH may be prepared according to the general scheme 2.

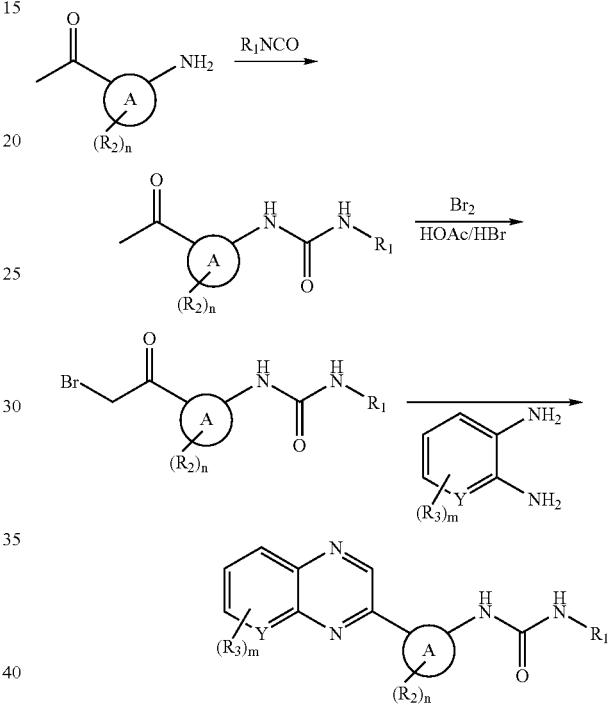

Scheme 2

Amine starting material is treated with the appropriate isocyanate R$_1$—NCO to form the desired urea. The resulting compound is then alpha brominated with Br$_2$ in a mixture of acetic and hydrobromic acids. This alpha-bromo ketone is converted to the final quinoxaline or 5-azaquinoxaline product by reacting with the appropriate 1,2-phenylenediamine or 2,3-pyridinediamine in the presence of a base such as sodium acetate. The same scheme may be used to prepare thiourea compounds of the invention, i.e. X is NR$_4$C(S)NH, by employing an appropriate isothiocyanate R$_1$—NCS in place of the isocyanate.

Compounds of the invention in which X is NR$_4$SO$_2$ may be prepared according to the general scheme 3.

Scheme 3

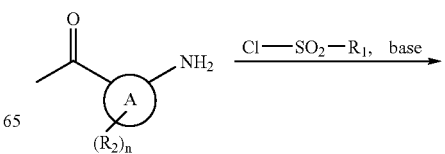

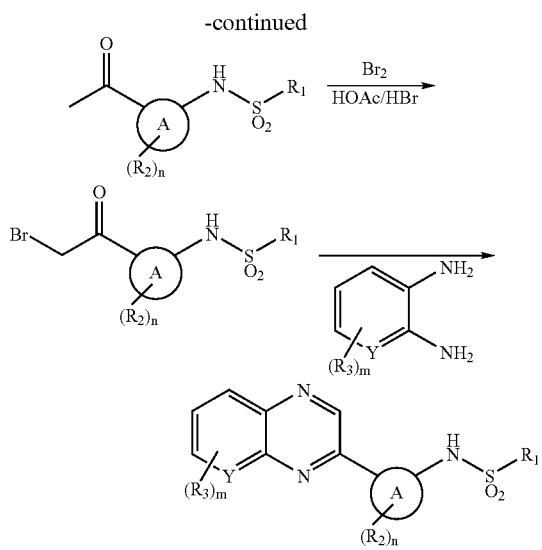

Amine starting material is treated with the appropriate sulfonyl chloride $R_1$—$S(O_2)Cl$ in the presence of a non-nucleophilic base such as triethylamine or diisopropylethylamine to form the desired sulfonamide. The resulting compound is then alpha brominated with $Br_2$ in a mixture of acetic and hydrobromic acids. This alpha-bromo ketone is converted to the final quinoxaline or 5-azaquinoxaline product by reacting with the appropriate 1,2-phenylenediamine or 2,3-pyridinediamine in the presence of a base such as sodium acetate.

The compounds of the invention inhibit the hedgehog signaling and are useful for the treatment of cancers associated with aberrant hedgehog signaling, for example when Patched fails to, or inadequately, represses Smoothened (Ptc loss-of-function phenotype) and/or when Smoothened is active regardless of Patched repression (Smo gain-of-function phenotype). Examples of such cancer types include basal cell carcinoma, neuroectodermal tumors such as medullablastoma, meningioma, hemangioma, glioblastoma, pancreatic adenocarcinoma, squamous lung carcinoma, chondrosarcoma, breast carcinoma, rhabdomyosarcoma, oesophageal cancer, stomach cancer, biliary tract cancer, renal carcinoma, thyroid carcinoma. Compounds of the invention may be administered prior to, concomitantly with, or following administration of other anticancer treatments such as radiation therapy or chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphteria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present invention are coadministered with a cytostatic compound selected from the group consisting of cisplatin, doxorubicin, taxol, taxotere and mitomycin C.

Another class of active compounds which can be used in the present invention are those which are able to sensitize for or induce apoptosis by binding to death receptors ("death receptor agonists"). Such agonists of death receptors include death receptor ligands such as tumor necrosis factor a (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. In a particular embodiment, the death receptor ligand is TNF-α. In another particular embodiment the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration including the location of the tumor in relation to other organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional confommal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention. Furthermore, the present invention encompasses types of non-ionizing radiation like e.g. ultraviolet (UV)

radiation, high energy visible light, microwave radiation (hyperthermia therapy), infrared (IR) radiation and lasers. In a particular embodiment of the present invention UV radiation is applied.

Compounds of the invention inhibit angiogenesis and are therefore useful in the treatment of diseases or conditions mediated by angiogenesis such as tumors, in particular solid tumors such as colon, lung, pancreatic, ovarian, breast and glioma. Furthermore, compounds of the invention are useful for treating macular degeneration e.g. wet age-related macular degeneration. Compounds of the invention are also useful for treating inflammatory/immune diseases such as Crohn's, inflammatory bowel disease, Sjogren's syndrome, asthma, organ transplant rejection, systemic lupus erythmatoses, rheumatoid arthritis, psoriatic arthritis, psoriasis and multiple sclerosis. Compounds of the invention are also useful as a depilatory.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of the invention used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but may range from about 3 to about 8. A particular formulation is an acetate buffer at pH 5. The inhibitory compound for use herein may be in a sterile formulation. The compound may be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to decrease hedgehog pathway signaling or else is the minimum amount necessary to cause reduction in size, volume or mass of a tumor that is responsive to hedgehog signaling, or a reduction in the increase in size, volume or mass of such a tumor. Alternatively "effective amount" of the compound means the amount necessary to reduce the number of malignant cells or the rate in increase of the number of malignant cells. Alternatively, "effective amount" is the amount of the compound of the invention required to increase survival of patients afflicted with an anti-hedgehog pathway sensitive tumor. Such amount may be below the amount that is toxic to normal cells, or the mammal as a whole. With respect to non-malignant indications, "effective amount" means the amount of compound of the invention required to decrease severity of the particular indication or symptoms thereof.

Generally, the initial pharmaceutically effective amount of the compound of the invention administered parenterally per dose will be in the range of about 0.01 to about 100 mg/kg, for example about 0.1 to about 20 mg/kg of patient body weight per day, for example about 0.3 to about 15 mg/kg/day. Oral unit dosage forms, such as tablets and capsules, may contain from about 25 to about 1000 mg of the compound of the invention.

The compound of the invention may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants. Topical formulations include ointments, creams, lotions, powders, solutions, pessaries, sprays, aerosols and capsules. Ointments and creams may be formulated with an aqueous or oily base with the addition of suitable thickening and/or gelling agents and/or solvents. Such bases may include water and/or an oil such a liquid paraffin or a vegetable oil such as arachis oil or castor oil or a solvent such as a polyethylene glycol. Thickening agents which may be used include soft paraffin, aluminum stearate, cetostearyl alcohol, polyethylene glycols, microcrystalline wax and beeswax. Lotions may be formulated with an aqueous or oily base and may contain one or more emulsifying agents, stabilizing agents, dispersing agents, suspending agents or thickening agents. Powders for external application may be formed with the aid of any suitable powder base e.g. talc, lactose or starch. Drops may be formulated with an aqueous or non-aqueous base also comprising one or more dispersing agents, solubilizing agents or suspending agents.

EXAMPLES

The invention will be more fully understood by reference to the following examples. They should not, however, be construed as limiting the scope of the invention. Abbreviations used herein are as follows:
DIPEA: diisopropylethylamine;
DMAP: 4-dimethylaminopyridine;
DME: 1,2-dimethoxyethane;
DMF: dimethylformamide;
EDC: 1-ethyl-3-(3-dimethylaminopropyl)carbodiimide;
HATU: O-(7-Azobenzotriazol-1-yl)-1,1,3,3-tetramethyluronium hexafluorophosphate;
HOAc: acetic acid
HOBt: hydroxybenzotriazole
NBS: N-bromosuccinamide;
ROESY: Rotating frame Overhauser Effect SpectroscopY
TASF: tris(dimethylamino)sulfonium difluorotrimethylsilicate;
THF: tetrahydrofuran;

All reagents were obtained commercially unless otherwise noted. Reactions were performed using oven-dried glassware under an atmosphere of nitrogen. Air and moisture sensitive liquids and solutions were transferred via syringe or stainless steel cannula. Organic solutions were concentrated under reduced pressure (ca. 15 mm Hg) by rotary evaporation. Unless otherwise noted all solvents were used obtained commercially. Chromatographic purification of products was accomplished by use of an Isco CombiFlash Companion and media. Reaction times are given for illustration only. The course of reactions was followed by thin-layer chromatography (TLC) and liquid chromatography-mass spectrometry (LC-MS). Thin-layer chromatography (TLC) was performed on EM Science silica gel 60 $F_{254}$ plates (250 µm). Visualization of the developed chromatogram was accomplished by fluorescence quenching. LC-MS were acquired with a Shimadzu 10AD LC on a Phenomenex column (50×4.6 mm, 5 µm) operating at 3 mL/min. A Shimadzu SPD-10A detector monitoring at 214 and 254 nm was used. Single quadrupole mass spectrometry was performed on an Applied Biosystems mass spectrometer. Nuclear magnetic resonance (NMR) spectra were acquired on a Varian Inova spectrometer operating at 400 MHz for $^1$H and are referenced internally to tetramethylsilane (TMS) in parts per million (ppm). Data for $^1$H NMR are recorded as follows: chemical shift (δ, ppm), multiplicity (s, singlet; bs, broad singlet; d, doublet; t, triplet; q, quartet; quint, quintet; sext, sextet; hept, heptet; m, multiplet; bm, broad multiplet), and integration. The structure and purity of all final products were assessed by at least one of the following techniques: LC-MS, NMR, TLC.

Example 1

General Procedure

Compounds of examples 2-11 were prepared according to the following general procedure.

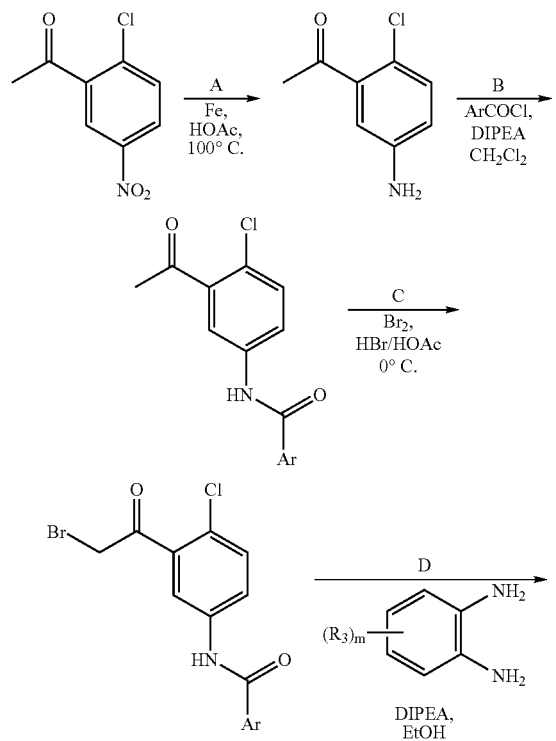

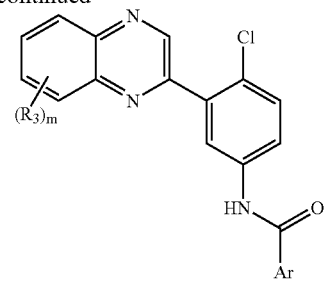

A: Reduction Procedure

To a magnetically stirred solution of the appropriate nitroaromatic (1 eq) in 10 ml of HOAc was added 325 mesh iron powder (10 eq) in a single portion. The resulting suspension was heated to 120° C. for 30 minutes, then poured into ice. The resulting solution was extracted with EtOAc (3×20 ml). The combined organics were washed with saturated $NaHCO_3$ (3×10 ml), dried with solid anhydrous $MgSO_4$, then concentrated. The crude product was purified by flash column chromatography to afford the desired aniline.

B: Acylation Procedure

To a magnetically stirred solution of the appropriate aniline (1 eq) in 20 ml of dichloromethane was added diisopropylethylamine (2.1 eq), followed by the appropriate acid chloride (1.4 eq) in a single portion. The reaction was stirred overnight at room temperature. The resulting solution was stirred an additional 3 h, and then quenched by the addition of 30 ml 1N HCl. The layers were separated and the aqueous layer was extracted with EtOAc (3×30 ml). The combined organics were washed with saturated $NaHCO_3$ (1×20 ml), dried with solid anhydrous $MgSO_4$, then concentrated. The crude product was purified by flash column chromatography to afford the desired amide.

C: Bromination Procedure

To a magnetically stirred solution of the appropriate acetophenone (1 eq) in 1 ml of benzene at 0° C. was added 1 ml 30% HBr in HOAc slowly, maintaining the temperature. $Br_2$ (1.1 eq) was then added dropwise, and the resultant solution stirred at 0° C. for 1 h. The reaction was poured onto ice, and the solution neutralized with solid $NaHCO_3$, then extracted with EtOAc (3×10 ml). The combined organics were dried with solid anhydrous $MgSO_4$, then concentrated. The resulting α-bromoacetophenone was carried on to the next reaction without purification.

D: Quinoxaline Formation Procedure

To a magnetically stirred solution of the appropriate α-bromoacetophenone (1 eq) in 5 ml of ethanol was added the appropriate 1,2-phenylenediamine (2.7 eq), followed by DIPEA (3.4 eq). The resultant solution was stirred at room temperature overnight with an air atmosphere. The reaction was concentrated, then purified by reverse phase chromatography on a C-18 column using a 0 to 90% gradient of $CH_3CN$ in water, with both containing 0.05% TFA. Product containing fractions were lyophilized to give a powder.

Example 2

N-(4-chloro-3-(quinoxalin-3-yl)phenyl)-3,5-dimethoxybenzamide

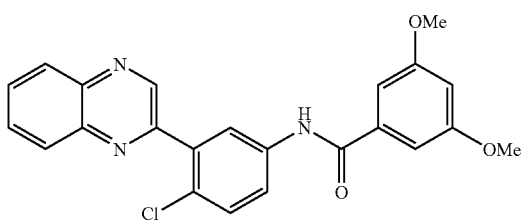

Procedure A was performed with 2'-chloro-5'-nitro-acetophenone (0.22 g, 1.1 mmol) and iron powder (0.64 g, 11 mmol). The crude product was purified by flash column chromatography on silica gel eluting with EtOAc:hexanes (0:1 to 1:0) to afford the desired 2'-chloro-5'-amino-acetophenone.

To a magnetically stirred solution of 2'-chloro-5'-amino-acetophenone (0.72 g, 4.2 mmol) in 20 ml of dichloromethane was added diisopropylethylamine (2.2 ml, 12.6 mmol). 3,5-dimethoxybenzoyl chloride (1.39 g, 6.9 mmol) in a single portion. The reaction was stirred for 2 h at room temperature, and a second portion of 3,5-dimethoxybenzoyl chloride (1.26 g, 6.3 mmol) was added, followed by diisopropylethylamine (1.0 ml, 5.7 mmol). The resulting solution was stirred an additional 3 h, and then quenched by the addition of 30 ml 1N HCl. The layers were separated and the aqueous layer was extracted with EtOAc (3×30 ml). The combined organics were washed with saturated NaHCO$_3$ (1×20 ml), dried with solid anhydrous MgSO$_4$, then concentrated. The crude product was purified by flash column chromatography on silica gel eluting with EtOAc:hexanes (0:1 to 2:5) to afford the desired N-(3-acetyl-4-chlorophenyl)-3,5-dimethoxybenzamide.

Procedure C was performed using N-(3-acetyl-4-chlorophenyl)-3,5-dimethoxybenzamide (0.1 g, 0.3 mmol) and Br$_2$ (0.017 ml, 0.33 mmol to afford N-(3-(2-bromoacetyl)-4-chlorophenyl)-3,5-dimethoxybenzamide.

Procedure D was performed using N-(3-(2-bromoacetyl)-4-chlorophenyl)-3,5-dimethoxybenzamide (0.029 g, 0.07 mmol), 1,2-phenylenediamine (0.021 g, 0.19 mmol) and DIPEA (0.042 ml, 0.24 mmol) to give N-(4-chloro-3-(quinoxalin-3-yl)phenyl)-3,5-dimethoxybenzamide as a light tan powder.

$^1$H NMR (CDCl$_3$, 400 MHz) δ 9.26 (s, 1H), 8.15-8.18 (m, 2H), 7.91-7.92 (m, 2H), 7.80-7.82 (m, 2H), 7.54 (d, 1H), 6.96 (d, 2H), 6.61 (t, 1H), 3.83 (s, 6H) ppm); MS (Q1) XXX (M)$^+$.

Example 3

N-(4-chloro-3-(6-methylquinoxalin-2-yl)phenyl)-3,5-dimethoxybenzamide

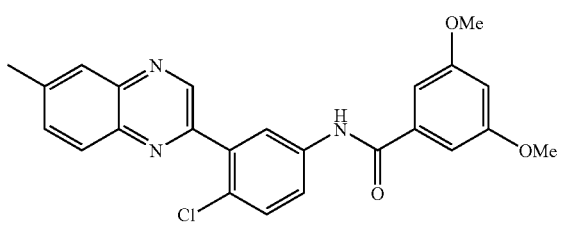

Procedure D was performed using N-(3-(2-bromoacetyl)-4-chlorophenyl)-3,5-dimethoxybenzamide (0.045 g, 0.11 mmol), 4-methyl-1,2-phenylenediamine (0.022 g, 0.18 mmol) and DIPEA (0.06 ml, 0.34 mmol). The resulting N-(4-chloro-3-(6-methylquinoxalin-2-yl)phenyl)-3,5-dimethoxybenzamide was a light powder and consisted of a mixture of the 6- and 7-methylated products.

$^1$H NMR (CDCl$_3$, 400 MHz) δ 9.21 (s, 1H), 8.08 (d, 1H), 7.90-7.96 (m, 3H), 7.68 (d, 1H), 7.56 (d, 1H), 6.98 (d, 2H), 6.64 (t, 1H), 3.83 (s, 6H) ppm); MS (Q1) 434.3 (M)$^+$.

Example 4

N-(4-chloro-3-(5,7-dimethylquinoxalin-3-yl)phenyl)-3,5-dimethoxybenzamide

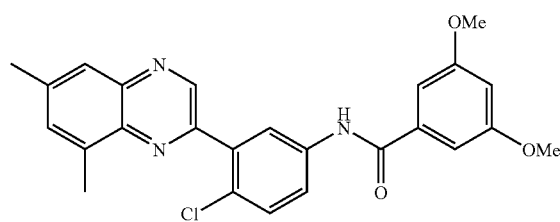

Procedure D was performed using N-(3-(2-bromoacetyl)-4-chlorophenyl)-3,5-dimethoxybenzamide (0.044 g, 0.11 mmol), 3,5-dimethyl-1,2-phenylenediamine (0.020 g, 0.18 mmol) and DIPEA (0.06 ml, 0.34 mmol). The resulting N-(4-chloro-3-(5,7-dimethylquinoxalin-3-yl)phenyl)-3,5-dimethoxybenzamide was a light powder whose regiochemistry was determined by analogy to example 10.

$^1$H NMR (CDCl$_3$, 400 MHz) δ 9.22 (s, 1H), 7.95 (d, 1H), 7.86-7.90 (m, 2H), 7.78 (br s, 1H), 7.56 (d, 1H), 7.51 (br s, 1H), 6.79-7.00 (m, 2H), 6.62-6.66 (m, 1H), 3.86 (s, 6H), 2.82 (s, 3H), 2.59 (s, 3H) ppm; MS (Q1) 448.0 (M)$^+$.

Example 5

N-(4-chloro-3-(5-methylquinoxalin-3-yl)phenyl)-3,5-dimethoxybenzamide

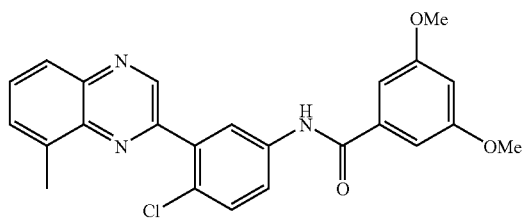

Procedure D was performed using N-(3-(2-bromoacetyl)-4-chlorophenyl)-3,5-dimethoxybenzamide (0.023 g, 0.06 mmol), 2,3-diaminotoluene (0.027 g, 0.22 mmol) and DIPEA (0.05 ml, 0.30 mmol). N-(4-chloro-3-(5-methylquinoxalin-3-yl)phenyl)-3,5-dimethoxybenzamide was a light powder whose regiochemistry was determined by analogy to example 10.

¹H NMR (CDCl₃, 400 MHz) δ 9.26 (s, 1H), 8.00-8.03 (m, 1H), 7.96 (d, 1H), 7.89-7.91 (m, 1H), 7.85 (dd, 1H), 7.65-7.74 (m, 2H), 7.514 (d, 1H), 6.96-7.98 (m, 2H), 6.61-6.62 (m, 1H), 3.83 (s, 6H), 2.85 (s, 3H) ppm; MS (Q1) 434.0 (M)⁺.

Example 6

N-(4-chloro-3-(5,6-dimethylquinoxalin-3-yl)phenyl)-3,5-dimethoxybenzamide

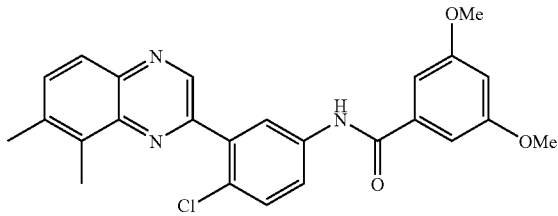

Procedure D was performed using N-(3-(2-bromoacetyl)-4-chlorophenyl)-3,5-dimethoxybenzamide (0.034 g, 0.08 mmol), 3,4-dimethylbenzene-1,2-diamine (0.017 g, 0.12 mmol) and DIPEA (0.042 ml, 0.24 mmol). N-(4-chloro-3-(5,6-dimethylquinoxalin-3-yl)phenyl)-3,5-dimethoxybenzamide was a light powder whose regiochemistry was determined by analogy to example 10.

¹H NMR (CDCl₃, 400 MHz) δ 9.26 (s, 1H), 8.00-8.03 (m, 1H), 7.96 (d, 1H), 7.89-7.91 (m, 1H), 7.85 (dd, 1H), 7.65-7.74 (m, 2H), 7.514 (d, 1H), 6.96-7.98 (m, 2H), 6.61-6.62 (m, 1H), 3.83 (s, 6H), 2.85 (s, 3H) ppm; MS (Q1) XXX (M)⁺.

Example 7

N-(4-chloro-3-(quinoxalin-3-yl)phenyl)-6-(trifluoromethyl)-2-methylpyridine-3-carboxamide

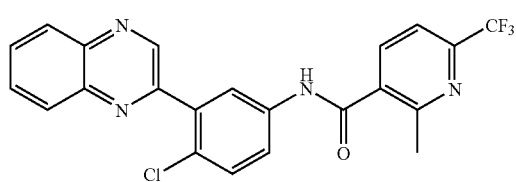

Procedure B was performed using 1-(5-amino-2-chlorophenyl)ethanone (0.4 g, 2.4 mmol), triethylamine (0.7 ml, 5.0 mmol) and 2-methyl-6-(trifluoromethyl)pyridine-3-carbonyl chloride (0.76 g, 3.4 mmol).

Procedure C was performed using N-(3-acetyl-4-chlorophenyl)-6-(trifluoromethyl)-2-methylpyridine-3-carboxamide (0.1 g, 0.3 mmol) and Br₂ (0.017 ml, 0.33 mmol to afford N-(3-(2-bromoacetyl)-4-chlorophenyl)-3,5-dimethoxybenzamide.

Procedure D was performed using N-(3-(2-bromoacetyl)-4-chlorophenyl)-6-(trifluoromethyl)-2-methylpyridine-3-carboxamide (0.029 g, 0.07 mmol), 1,2-phenylenediamine (0.021 g, 0.19 mmol) and DIPEA (0.042 ml, 0.24 mmol) to give N-(4-chloro-3-(quinoxalin-3-yl)phenyl)-3,5-dimethoxybenzamide as a light tan powder.

¹H NMR (CDCl₃, 400 MHz) δ 9.30 (s, 1H), 8.17-8.24 (m, 2H), 7.95-8.00 (m, 2H), 7.84-7.90 (m, 3H), 7.59-7.64 (m, 3H), 2.81 (s, 3H) ppm; MS (Q1) 443.1 (M)⁺.

Example 8

N-(4-chloro-3-(6-methylquinoxalin-2-yl)phenyl)-6-(trifluoromethyl)-2-methylpyridine-3-carboxamide

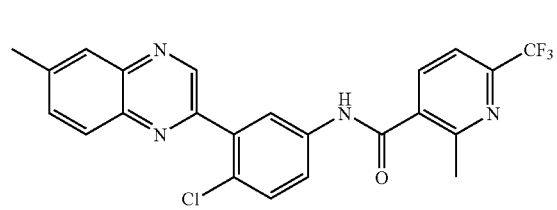

Procedure D was performed using N-(3-(2-bromoacetyl)-4-chlorophenyl)-6-(trifluoromethyl)-2-methylpyridine-3-carboxamide (0.042 g, 0.10 mmol), 4-methyl-1,2-phenylenediamine (0.025 g, 0.20 mmol) and DIPEA (0.052 ml, 0.30 mmol). The resulting N-(4-chloro-3-(6-methylquinoxalin-2-yl)phenyl)-6-(trifluoromethyl)-2-methylpyridine-3-carboxamide was a light powder and consisted of a mixture of the 6- and 7-methylated products.

¹H NMR (CDCl₃, 400 MHz) δ 9.22 (s, 1H), 8.09 (d, 1H), 7.86-7.98 (m, 4H), 7.77 (br s, 1H), 7.71 (d, 1H), 7.56-7.62 (m, 2H), 2.80 (s, 3H), 2.64 (s, 3H) ppm; MS (Q1) 457.1 (M)⁺.

Example 9

N-(4-chloro-3-(5,7-dimethylquinoxalin-3-yl)phenyl)-6-(trifluoromethyl)-2-methylpyridine-3-carboxamide

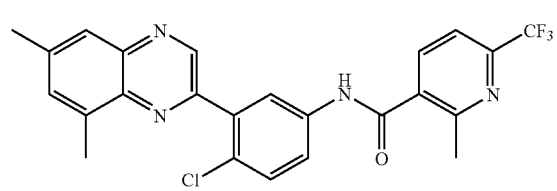

Procedure D was performed using N-(3-(2-bromoacetyl)-4-chlorophenyl)-6-(trifluoromethyl)-2-methylpyridine-3-carboxamide (0.038 g, 0.09 mmol), 3,5-dimethyl-1,2-phenylenediamine (0.029 g, 0.26 mmol) and DIPEA (0.052 ml, 0.30 mmol). The resulting N-(4-chloro-3-(5,7-dimethylquinoxalin-3-yl)phenyl)-6-(trifluoromethyl)-2-methylpyridine-3-carboxamide was a light powder whose regiochemistry was determined by analogy to example 10.

¹H NMR (DMSO, 400 MHz) δ 11.05 (s, 1H), 8.41 (s, 1H), 8.22 (d, 1H), 7.92 (d, 1H), 7.81-7.86 (m, 1H), 7.77 (d, 1H), 7.68 (d, 1H), 7.57 (br s, 1H), 6.81 (d, 1H), 2.66 (s, 3H), 2.51 (s, 3H); MS (Q1) XXX (M)⁺.

Example 10

N-(4-chloro-3-(5-methylquinoxalin-3-yl)phenyl)-6-(trifluoromethyl)-2-methylpyridine-3-carboxamide

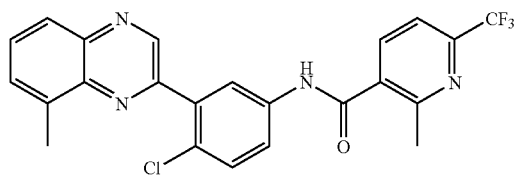

Procedure D was performed using N-(3-(2-bromoacetyl)-4-chlorophenyl)-6-(trifluoromethyl)-2-methylpyridine-3-carboxamide (0.026 g, 0.06 mmol), 2,3-diaminotoluene (0.018 g, 0.15 mmol) and DIPEA (0.05 ml, 0.30 mmol). N-(4-chloro-3-(5-methylquinoxalin-3-yl)phenyl)-6-(trifluoromethyl)-2-methylpyridine-3-carboxamide was a powder whose regiochemistry was determined by observation of transfer of magnetization from the quinoxaline methyl to the proton in the 2-position of the central phenyl ring and no transfer to the proton in the quinoxaline 2-position during the course of a ROESY experiment.

¹H NMR (CDCl₃, 400 MHz) δ 9.26 (s, 1H), 8.00-8.03 (m, 1H), 7.96 (d, 1H), 7.89-7.91 (m, 1H), 7.85 (dd, 1H), 7.65-7.74 (m, 2H), 7.514 (d, 1H), 6.96-7.98 (m, 2H), 6.61-6.62 (m, 1H), 3.83 (s, 6H), 2.85 (s, 3H) ppm; MS (Q1) 457.1 (M)⁺.

Example 11

N-(4-chloro-3-(5,6-dimethylquinoxalin-3-yl)phenyl)-6-(trifluoromethyl)-2-methylpyridine-3-carboxamide

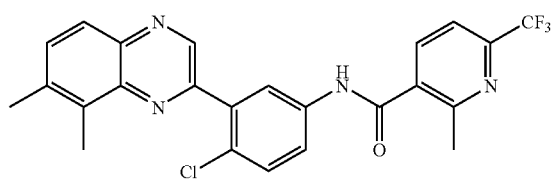

Procedure D was performed using N-(3-(2-bromoacetyl)-4-chlorophenyl)-6-(trifluoromethyl)-2-methylpyridine-3-carboxamide (0.018 g, 0.04 mmol), 3,4-dimethylbenzene-1,2-diamine (0.01 g, 0.07 mmol) and DIPEA (0.052 ml, 0.3 mmol). N-(4-chloro-3-(5,6-dimethylquinoxalin-3-yl)phenyl)-6-(trifluoromethyl)-2-methylpyridine-3-carboxamide was a light powder whose regiochemistry was determined by analogy to example 10.

¹H NMR (CDCl₃, 400 MHz) δ 9.18 (s, 1H), 7.89-7.98 (m, 3H), 7.83-7.87 (m, 1H), 7.68 (br s, 1H), 7.64 (d, 1H), 7.64-7.61 (m, 2H), 2.78 (s, 3H), 2.75 (s, 3H), 2.54 (s, 3H) ppm; MS (Q1) 471.3 (M)⁺.

Example 12

General Procedure

Compound of example 13 was prepared according to the following general procedure.

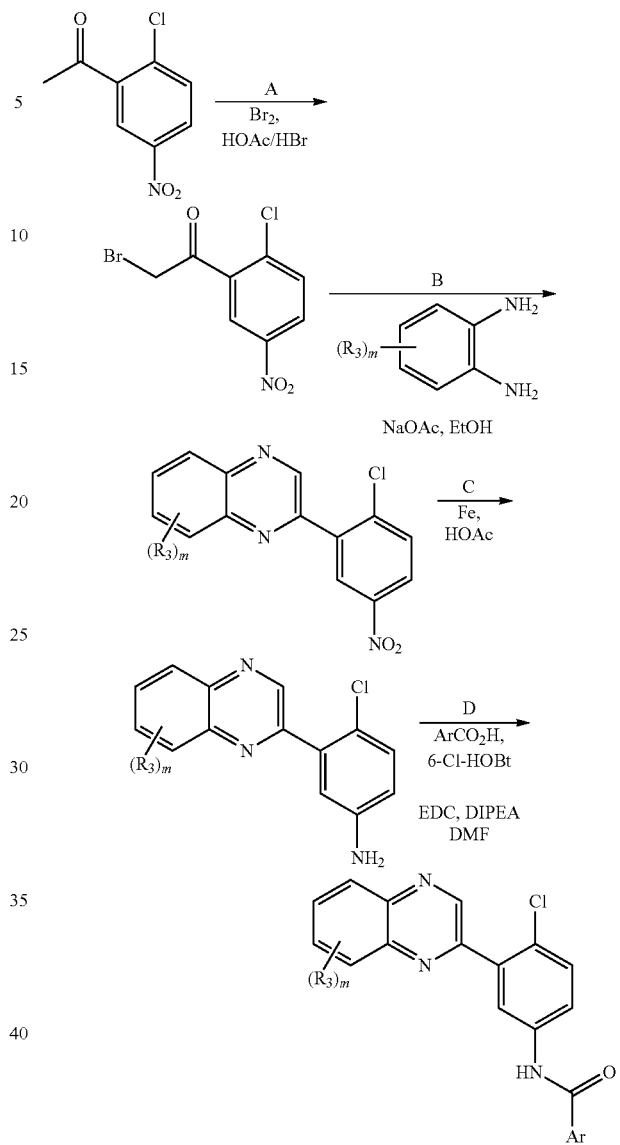

A: Bromination Procedure

To a magnetically stirred solution of the appropriate acetophenone (1 eq) in 40 ml of benzene at 0° C. was added 40 ml 30% HBr in HOAc slowly, maintaining the temperature. Br₂ (1.05 eq) was then added dropwise, and the resultant solution stirred at 0° C. for 15 min. The reaction was poured onto ice, and then extracted with EtOAc (3×30 ml). The combined organics were dried with solid anhydrous MgSO₄, then concentrated. The resulting crude alpha-bromoacetophenone was purified by flash column chromatography.

B: Quinoxaline Formation Procedure

To a magnetically stirred solution of the appropriate alpha-bromoacetophenone (1 eq) in 200 ml of ethanol was added the appropriate 1,2-phenylenediamine (2.4 eq), followed by addition of solid sodium acetate (3 eq). The resultant solution was warmed to reflux and stirred overnight with an air atmosphere. The product formed precipitates, and so the reaction was vacuum filtered, and the solids washed with 50 ml cold ethanol followed by washing with 50 ml 0.1 N HCl. The product was carried on without further purification.

C: Reduction Procedure

To a magnetically stirred suspension of the appropriate nitroaromatic (1 eq) in 100 ml of HOAc was added 325 mesh iron powder (3 eq) in a single portion. The resulting suspension was stirred at room temperature for 1 h, during which time the organics dissolved completely, forming a dark red solution. The reaction is then poured into ice, and the resulting solution was extracted with EtOAc (3×200 ml). The combined organics were washed with saturated $NaHCO_3$ (3×200 ml), dried with solid anhydrous $MgSO_4$, then concentrated. The crude product was purified by flash column chromatography to afford the desired aniline.

D: Acylation Procedure

To a magnetically stirred solution of the appropriate acid (1.05 eq) in 20 ml of DMF was added EDC (2.0 eq) and DIPEA (2.0 eq), followed by 6-chloro-hydroxybenzotriazole (2 eq). The resulting solution was stirred for 30 minutes at room temperature, then the appropriate aniline was added and stirring was continued overnight at room temperature. The reaction was diluted with 100 ml of water and extracted with EtOAc (3×50 ml). The combined organics were washed with water (3×100 ml), dried with solid anhydrous $MgSO_4$, then concentrated. The crude product was purified by flash column chromatography to afford the desired amide.

Example 13

N-(4-chloro-3-quinoxalin-2-yl-phenyl)-4-methane-sulfonyl-benzamide

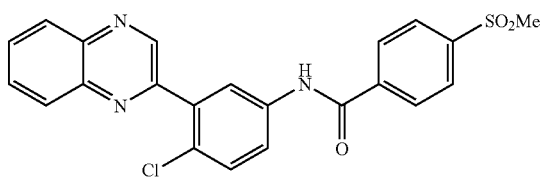

Procedure A was performed with 2'-chloro-5'-nitro-acetophenone (4.0 g, 20 mmol) and bromine (1.13 ml, 22 mmol). The crude product was purified by flash column chromatography on silica gel eluting with EtOAc:hexanes (0:1 to 1:4) to afford the desired 2-bromo-2'chloro-5'-nitroacetophenone (5.4 g, 19.2 mmol).

Procedure B was performed with 2-bromo-2'chloro-5'-nitroacetophenone (14.16 g, 50 mmol), 1,2-phenylenediamine (13.1 g, 120 mmol) and NaOAc (12.4, 150 mmol) to give the desired 2-(2-chloro-5-nitro-phenyl)-quinoxaline (8.6 g, 30 mmol).

Procedure C was performed using quinoxaline (8.6 g, 30 mmol) and Fe (5.2 g, 90 mmol) to afford aniline (5.3 g, 20.7 mmol).

Procedure D was performed using 4-(methylsulfonyl)benzoic acid (102 mg, 0.49 mmol), EDC (186 mg, 0.93 mmol), DIPEA (0.16 ml, 0.93 mmol), 6-chloro-hydroxybenzotriazole (162 mg, 0.93 mmol) and aniline (119 mg, 0.46 mmol). The crude product was purified by flash column chromatography on silica gel eluting with EtOAc:hexanes (0:1 to 3:2) to afford the desired 4-chloro-3-quinoxalin-2-yl-phenylamine (104 mg, 0.24 mmol).

$^1$H NMR ($D_6$-DMSO, 300 MHz) δ 10.81 (s, 1H), 9.25 (s, 1H), 8.23-8.15 (m, 4H), 8.11-8.00 (m, 3H), 7.97-7.90 (m, 2H), 7.69 (s, 1H), 3.30 (s, 3H) ppm; MS (Q1) 438.0 $(M)^+$.

Example 14

Hedgehog Signalling Inhibition Assays

Mouse Reporter Cell lines—10T1/2-GliLuc [s12] cells (derived from cell line C3H10T1/2 ATCC #CCL-226); Mouse Embryonic Fibroblasts); Growth Medium: Dulbecco's modified Eagles' Medium (DMEM) supplemented with 10% Fetal Bovine Serum (FBS), 10 units/mL penicillin, 100 ug/mL streptomycin, 2 mM glutamine, and 10 mM HEPES.

Human Reporter Cell lines—HEPM-GliLuc [MZ24]—cells (derived from HEPM, Human Embryonic Palatal Mesenchyme ATCC #CRL-1486); Growth Medium: Minimum Essential Medium (MEM; with Earle's salts) supplemented with 10-20% Fetal Bovine Serium (FBS), 10 units/mL penicillin, 100 ug/mL streptomycin, 2 mM glutamine, and 10 mM HEPES pH 7.2.

Sonic hedgehog—recombinant human SHh N-terminal octylated conjugate.

Microtiter Plates (MTPs)—For the Luciferase assay cells are plated in 96-well MTPs (White, Flat-bottom, Clear-View).

Luciferase-Assay Medium—DMEM supplemented with 0.5% FBS, 10 units/mL penicillin, 100 ug/mL streptomycin, 2 mM glutamine, and 10 mM HEPES pH 7.2.

PBS/Ca/Mg Mix—Phosphate Buffered Saline (PBS) supplemented with 0.5 mM $CaCl_2$ and 1 mM $MgCl_2$.

Assay Procedure

S12 and MZ24 cells genetically modified to contain a luciferase reporter gene driven by the hedgehog-responsive Gli promoter were maintained on tissue culture dishes in Growth Medium at 37° C. and 5% $CO_2$. Cell cultures were passaged at sub-confluency at every 3-4 days. (1:20 to 1:40 for s12; 1:3 to 1:10 for MZ24). Cells were harvested and diluted in Growth Medium such that they could be plated in a microtitre plate at 10,000-20,000 cells (s12), or 20,000-30,000 cells (MZ24), per 100 ul, per well. Cells were further incubated for ~24-48 hours at 37° C. and 5% $CO_2$.

After ~24-48 hour incubation the Growth Medium in the microtitre plates was replaced by Luciferase-Assay Medium (100 ul per well), with and without Sonic hedgehog-octyl conjugate, at 0.1-0.3 ug/ml (S12) or 0.5-1.0 ug/ml (MZ24), and test compounds. Cells were then further incubated for and additional 24 hrs.

Microtitre plates were then subjected to the luciferase reporter gene assay kit (LucLite™), with modifications to the manufacturer's procedure wherein medium was removed and the substrate was reconstituted with 1:1 PBS/Ca/Mg:lysis buffer instead of straight lysis buffer. In brief, the PBS/Ca/Mg was mixed 1:1 with lysis buffer and 10 mL were added to each substrate vial (of the 1000-assay kit). Then the assay media from the microtitre plate was discarded, and 100 ul of this substrate mix was added to each well. Plates were incubated at room temperature for 20-30 minutes and then the Relative Light Units (RLUS) representing the relative expression level of the luciferase reporter gene were determined with a Top-count reader (Packard) or an Analyst reader (Molecular Devices).

The following table 1 represents the average $IC_{50}$ values for particular compounds tested according to the procedures above using either mouse [s12] or human [MZ24] Gli reporter cell lines indicating inhibition of hedgehog pathway signaling.

TABLE 1

| compound | IC$_{50}$ (μM) | compound | IC$_{50}$ (μM) |
| --- | --- | --- | --- |
| 6 | <1 | 7 | <1 |
| 15 | <1 | 18 | <1 |
| 19 | <1 | 24 | <1 |
| 27 | <1 | 31 | <1 |
| 33 | <1 | 34 | <1 |
| 35 | <1 | 36 | <1 |
| 37 | <1 | 38 | <1 |
| 39 | <1 | 40 | <1 |
| 41 | <1 | 42 | <1 |
| 43 | <1 | 44 | <1 |
| 45 | <1 | 46 | <1 |
| 47 | <1 | 48 | <1 |
| 50 | <1 | 51 | 1 |
| 52 | <1 | 53 | <1 |
| 54 | <1 | 55 | <1 |
| 56 | <1 | | |

We claim:

1. A compound of formula I:

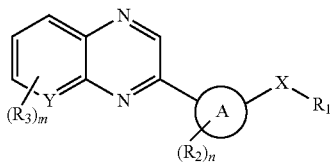

wherein
A is a carbocycle;
X is NR$_4$C(O), NR$_4$C(S), NR$_4$C(NH), NR$_4$SO, NR$_4$SO$_2$, NR$_4$C(O)NH, NR$_4$C(S)NH, C(O)NR$_4$, C(S)NR$_4$, C(NH)NR$_4$, or NR$_4$PO(OH) wherein R$_4$ is H or alkyl;
Y is N, CH or CR$_3$;
R$_1$ is selected from the group consisting of alkyl, cycloalkyl, aryl or a heterocycle each of which is optionally substituted with hydroxy, halogen, amino, nitro, alkyl, acyl, alkylsulfonyl, haloalkyl or alkoxy; and said cycloalkyl, aryl and heterocycle are optionally further substituted with —(CH$_2$)$_s$-(Q)$_u$-(CH$_2$)$_t$—Z wherein Q is C(O), S(O), SO$_2$, C(O)O, OC(O), NR$_4$C(O), NR$_4$C(S), NR$_4$SO, NR$_4$SO$_2$, NR$_4$C(O)NH, NR$_4$C(S)NH, C(O)NR$_4$, or C(S)NR$_4$; and Z is hydroxy, amino, halogen, alkylsulfonyl, alkoxy, alkoxycarbonyl, haloalkyl, a carbocycle, a heterocycle or a carbocycle or heterocycle substituted with hydroxy, halogen, amino, nitro, alkyl, acyl, alkylsulfonyl, haloalkyl, hydroxyalkyl, alkoxy or alkoxyalkoxy; and s and t are independently 0, 1, 2, 3, 4 or 5 and u is 0 or 1;
R$_2$ is halogen, hydroxy, alkyl, acyl or alkoxy each optionally substituted with hydroxy, halogen, amino, nitro, alkyl, acyl, alkylsulfonyl or alkoxy;
R$_3$ is halogen, hydroxy, alkyl, acyl or alkoxy each optionally substituted with hydroxy, halogen, amino, nitro, alkyl, acyl, alkylsulfonyl or alkoxy;
m is 0, 1, 2, or 3;
n is 1, 2 or 3;
or a pharmaceutically acceptable salt thereof.

2. The compound of claim 1, wherein X is NR$_4$SO$_2$.
3. The compound of claim 1, wherein R$_3$ is Me or F.
4. The compound of claim 1, wherein R$_3$ is Me and m is 1 or 2.
5. The compound of claim 1, wherein R$_3$ is F and m is 1 or 2.
6. The compound of claim 1, wherein m is 0.
7. The compound of claim 1, wherein m is 0.
8. The compound of claim 1, wherein X is NR$_4$C(O).
9. The compound of claim 1, wherein A is A$^2$:

wherein R$_2$ is halogen, hydroxy, alkyl or alkoxy; and n is 1, 2 or 3.

10. The compound of claim 9, wherein R$_2$ is Cl or Me.
11. The compound of claim 9, wherein A is A$^{2a}$

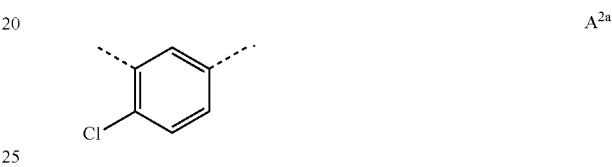

12. The compound of claim 9, wherein X is NR$_4$C(O).
13. The compound of claim 12, wherein R$_4$ is H or Me.
14. The compound of claim 13, wherein R$_4$ is H.
15. The compound claim 1, wherein R$_1$ is selected from the group consisting of formulae IIa, IIb, IIc, IId, IIe, IIf, IIg, IIh, IIi, IIj, IIk, IIl and IIm:

IIa

IIb

IIc

IId

IIe

IIf

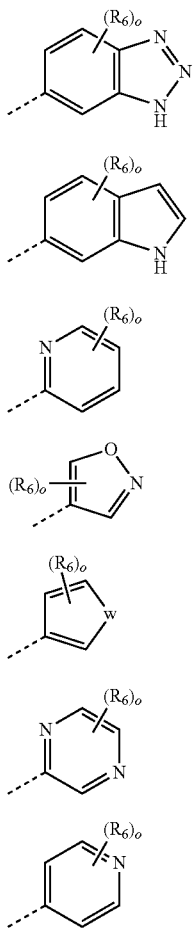

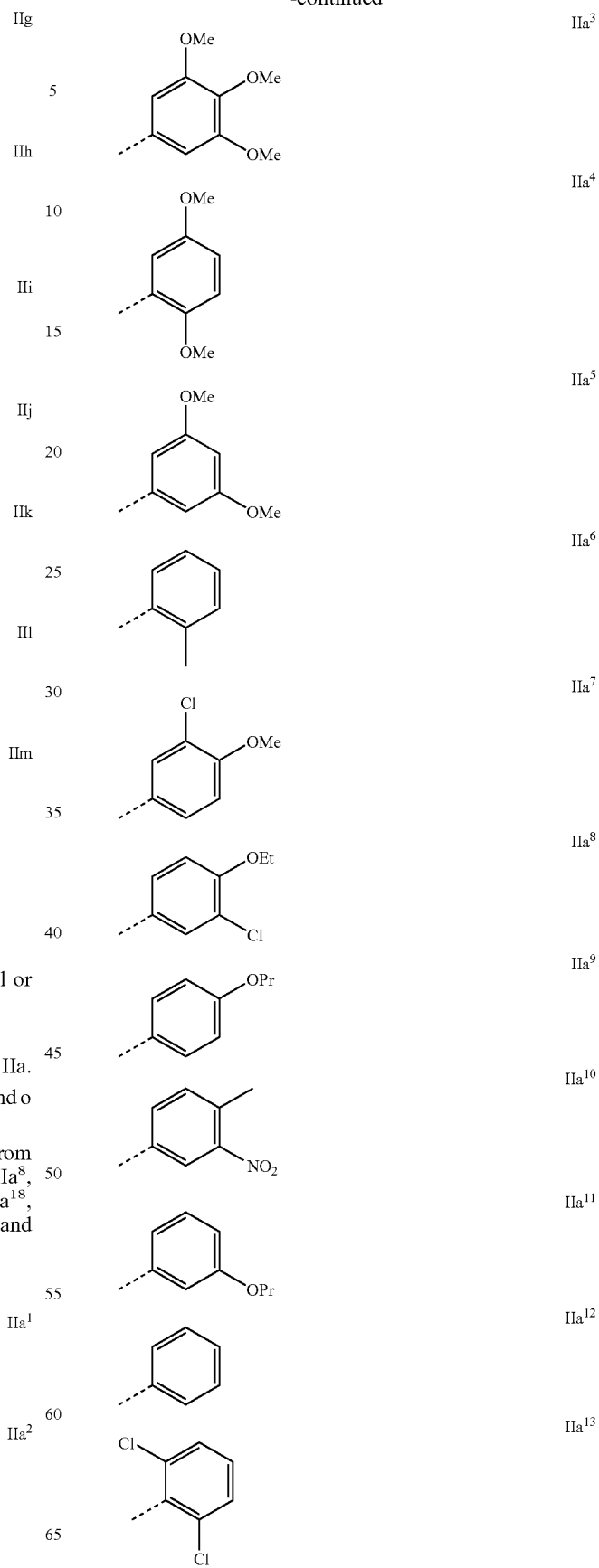

wherein

W is O, S or NR$_7$ wherein R$_7$ is H or alkyl;

R$_6$ is halogen, amino, nitro, alkyl, acyl, alkylsulfonyl or alkoxy; and o is 0, 1, 2 or 3.

16. The compound of claim 15, wherein R$_1$ is formula IIa.

17. The compound of claim 16, wherein R$_6$ is alkoxy and o is 1 or 2.

18. The compound of claim 16, wherein R$_1$ is selected from the group of formulae IIa$^1$, IIa$^2$, IIa$^3$, II$^4$ IIa$^5$, IIa$^6$, IIa$^7$, IIa$^8$, IIa$^9$, IIa$^{10}$, IIa$^{11}$, IIa$^{12}$, IIa$^{13}$, IIa$^{14}$, IIa$^{15}$, IIa$^{16}$, IIa$^{17}$, IIa$^{18}$, IIa$^{19}$, IIa$^{20}$, IIa$^{21}$, IIa$^{22}$, IIa$^{23}$, IIa$^{24}$, IIa$^{25}$, IIa$^{26}$, IIa$^{27}$ and IIa$^{28}$:

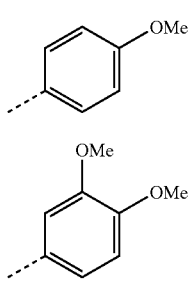

-continued

IIa¹⁴ 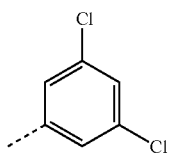

IIa¹⁵ 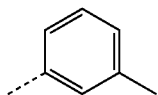

IIa¹⁶ 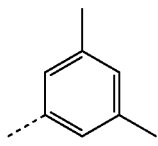

IIa¹⁷ 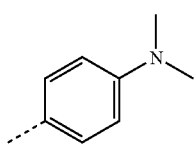

IIa¹⁸ 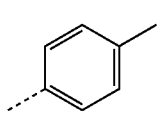

IIa¹⁹ 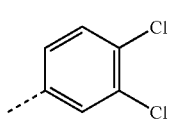

IIa²⁰ 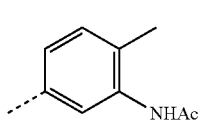

IIa²¹ 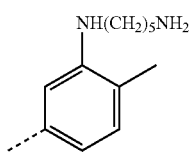

IIa²² 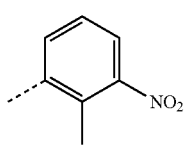

IIa²³ 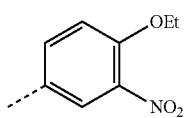

IIa²⁴ 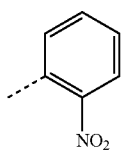

-continued

IIa²⁵ 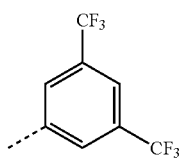

IIa²⁶ 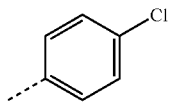

IIa²⁷ 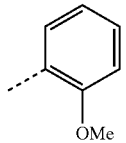

IIa²⁸ 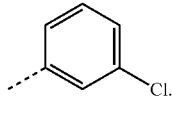

19. The compound of claim 16, wherein A is $A^2$:

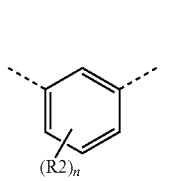

A² wherein $R_2$ is halogen, hydroxy, alkyl or alkoxy; and n is 1, 2 or 3.

20. The compound of claim 16, wherein $R_3$ is Me or F.

21. The compound of claim 15, wherein $R_1$ is of formula IIb.

22. The compound of claim 21, wherein $R_6$ is alkyl or haloalkyl.

23. The compound of claim 21, wherein $R_1$ is of formula IIb¹

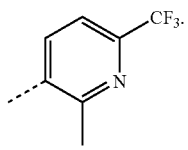

IIb¹

24. The compound of claim 21, wherein A is A2:

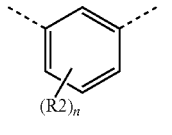

A² wherein $R_2$ is halogen, hydroxy, alkyl or alkoxy; and n is 1, 2 or 3.

25. The compound of claim 21, wherein $R_3$ is H, Me or F.

26. The compound of claim 21, wherein $R_3$ is H.

27. The compound of claim 21, wherein X is $NR_4C(O)$.

28. A pharmaceutically acceptable composition comprising a compound of claim 1 and a pharmaceutically acceptable carrier.

29. A method of inhibiting angiogenesis in a mammal, comprising administering to said mammal an effective amount of a compound of claim 1.

30. A method of treating cancer in a mammal, comprising administering to said mammal an effective amount of a compound of claim 1, wherein said cancer is basal cell carcinoma or medullablastoma.

31. A method of treating basal cell carcinoma in a mammal, comprising administering to said mammal an effective amount of a compound of claim 1.

* * * * *